(12) United States Patent
Malackowski et al.

(10) Patent No.: US 9,713,498 B2
(45) Date of Patent: Jul. 25, 2017

(54) ASSEMBLY FOR POSITIONING A STERILE SURGICAL DRAPE RELATIVE TO OPTICAL POSITION SENSORS

(71) Applicant: Stryker Corporation, Kalamazoo, MI (US)

(72) Inventors: Donald W. Malackowski, Schoolcraft, MI (US); José Luis Moctezuma de la Barrera, Freiburg (DE); Helmut Rohs, Freiburg (DE); Norbert Riedlinger, Riegel am Kaiserstuhl (DE)

(73) Assignee: STRYKER CORPORATION, Kalamazoo, MI (US)

( * ) Notice: Subject to any disclaimer, the term of this patent is extended or adjusted under 35 U.S.C. 154(b) by 301 days.

(21) Appl. No.: 14/212,871

(22) Filed: Mar. 14, 2014

(65) Prior Publication Data

US 2014/0261456 A1    Sep. 18, 2014

Related U.S. Application Data

(60) Provisional application No. 61/788,752, filed on Mar. 15, 2013.

(51) Int. Cl.
| | |
|---|---|
| A61B 19/02 | (2006.01) |
| A61B 19/08 | (2006.01) |
| A61B 90/00 | (2016.01) |
| A61B 46/10 | (2016.01) |
| A61B 50/00 | (2016.01) |
| A61B 34/20 | (2016.01) |
| A61B 17/00 | (2006.01) |

(52) U.S. Cl.
CPC ............ *A61B 19/081* (2013.01); *A61B 34/20* (2016.02); *A61B 46/10* (2016.02); *A61B 90/361* (2016.02); *A61B 50/00* (2016.02); *A61B 2017/00876* (2013.01); *A61B 2034/2055* (2016.02); *A61B 2034/2057* (2016.02); *A61B 2090/0808* (2016.02)

(58) Field of Classification Search
CPC ......... A61B 46/00; A61B 46/10; A61B 50/00; A61B 2050/005; A61B 2050/0058; A61B 2050/006; A61B 2050/0067; A61B 2050/0083; A61B 34/20; A61B 2034/2055; A61B 2034/2057; A61B 90/361
USPC .......... 128/849; 606/130; 359/507, 510, 511
See application file for complete search history.

(56) References Cited

U.S. PATENT DOCUMENTS

| | | |
|---|---|---|
| 5,490,524 A | 2/1996 | Williams et al. |
| 5,732,712 A | 3/1998 | Adair |
| 5,935,058 A | 8/1999 | Makita et al. |
| 6,132,368 A | 10/2000 | Cooper |

(Continued)

FOREIGN PATENT DOCUMENTS

WO    WO 99 42883 A1    8/1999

*Primary Examiner* — Keri J Nelson
(74) *Attorney, Agent, or Firm* — Howard & Howard Attorneys PLLC

(57) ABSTRACT

A camera and drape assembly for use with tracking elements of a surgical system includes a camera unit and a drape covering the camera unit. The camera unit includes a casing presenting a face for facing the tracking elements. Optical sensors are supported by the casing and are exposed through the casing for detecting the tracking elements. The drape covers the camera unit such that light signals from the tracking elements can be received by the optical sensors.

16 Claims, 15 Drawing Sheets

(56) References Cited

U.S. PATENT DOCUMENTS

| | | | |
|---|---|---|---|
| 6,679,267 | B2 | 1/2004 | McNeirney et al. |
| 7,182,474 | B2 | 2/2007 | Fuchs et al. |
| 7,666,191 | B2 | 2/2010 | Orban, III et al. |
| 7,699,855 | B2 | 4/2010 | Anderson et al. |
| 7,725,162 | B2 | 5/2010 | Malackowski et al. |
| 7,947,050 | B2 | 5/2011 | Lee et al. |
| 8,202,278 | B2 | 6/2012 | Orban, III et al. |
| 8,602,031 | B2 | 12/2013 | Reis et al. |
| 2002/0133058 | A1 | 9/2002 | Calderwood |
| 2007/0175486 | A1 | 8/2007 | Bogojevic et al. |
| 2008/0147089 | A1 | 6/2008 | Loh et al. |
| 2010/0076306 | A1 | 3/2010 | Daigneault |
| 2010/0268249 | A1 | 10/2010 | Stuart |
| 2012/0209291 | A1 | 8/2012 | Anderson et al. |
| 2012/0239060 | A1 | 9/2012 | Orban, III |
| 2012/0247489 | A1 | 10/2012 | Orban, III et al. |
| 2012/0305650 | A1* | 12/2012 | Prpa .................. G06K 7/10821 235/470 |
| 2014/0039681 | A1 | 2/2014 | Bowling et al. |

\* cited by examiner

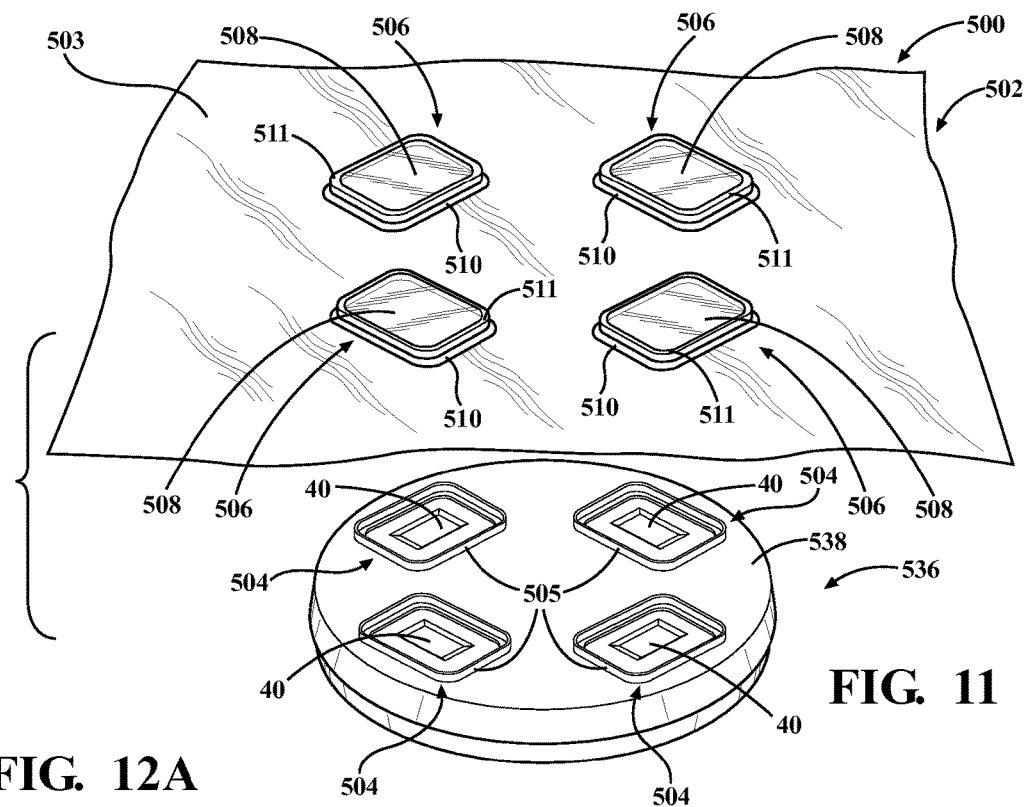
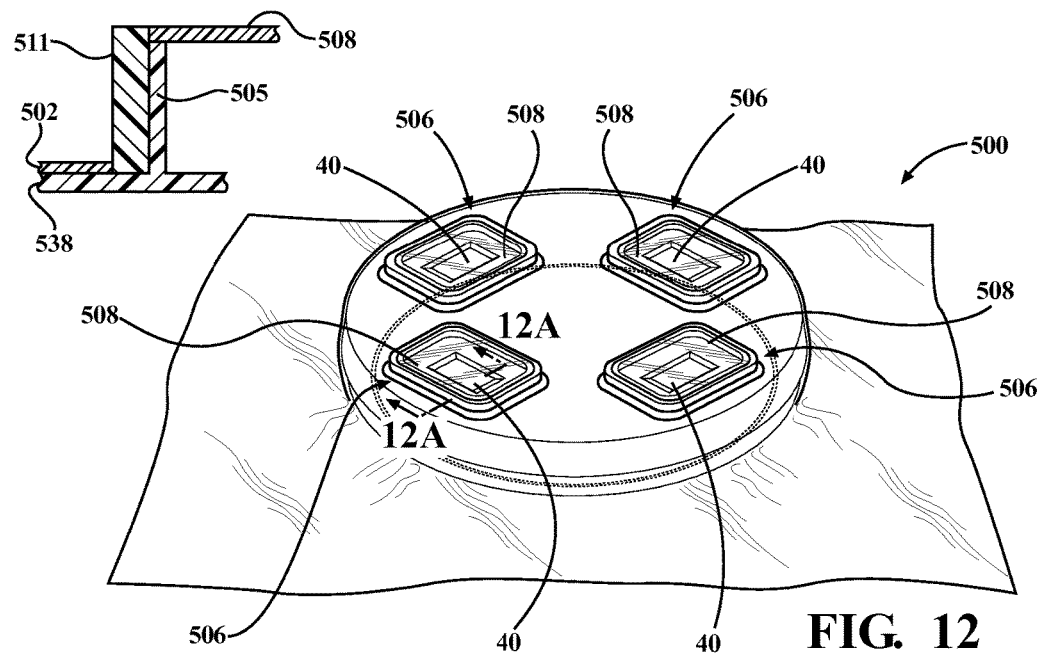
FIG. 11
FIG. 12A
FIG. 12

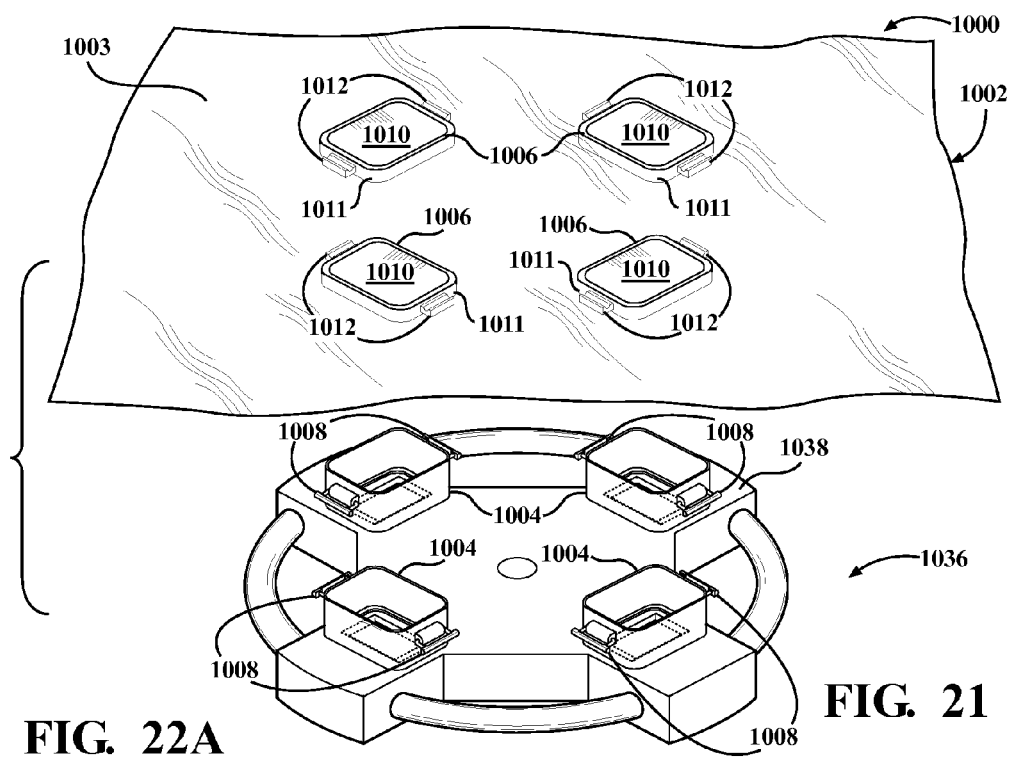
FIG. 21
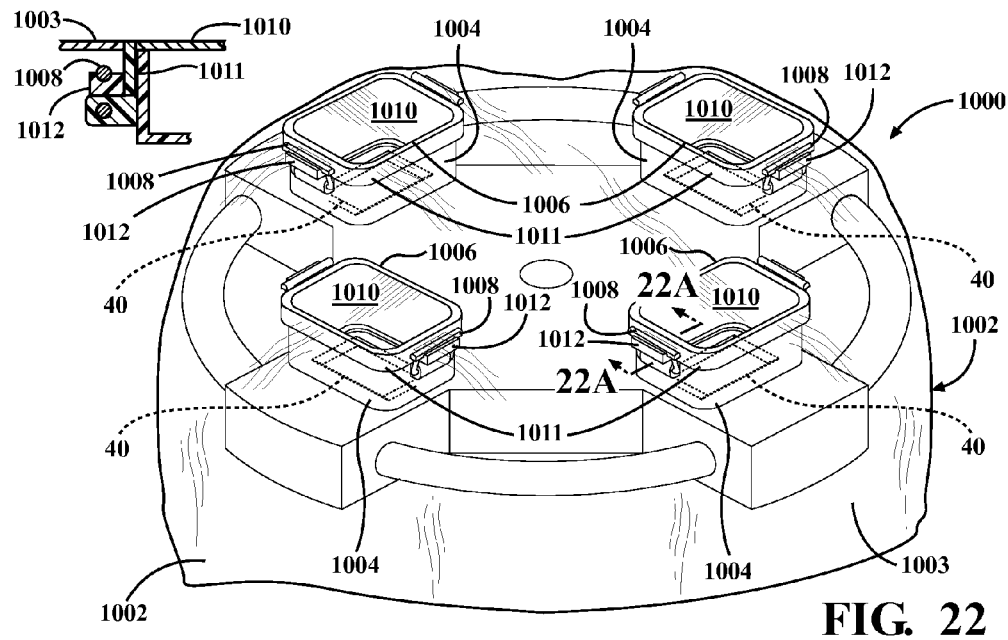
FIG. 22A
FIG. 22

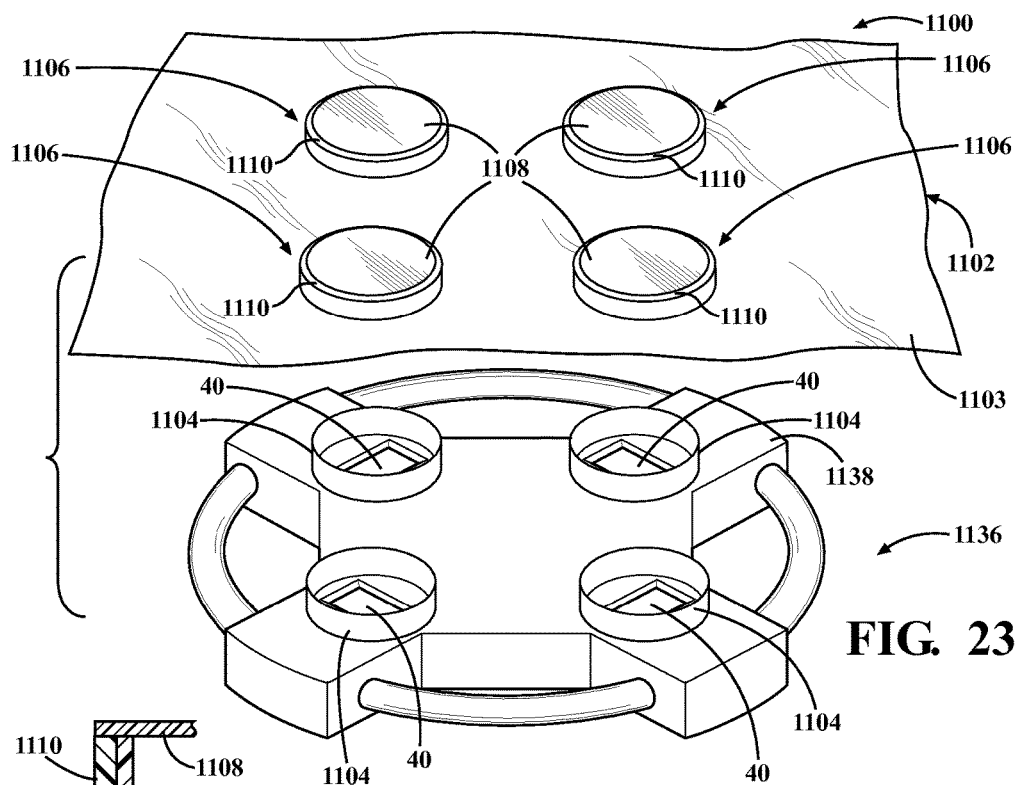
FIG. 23
FIG. 24A
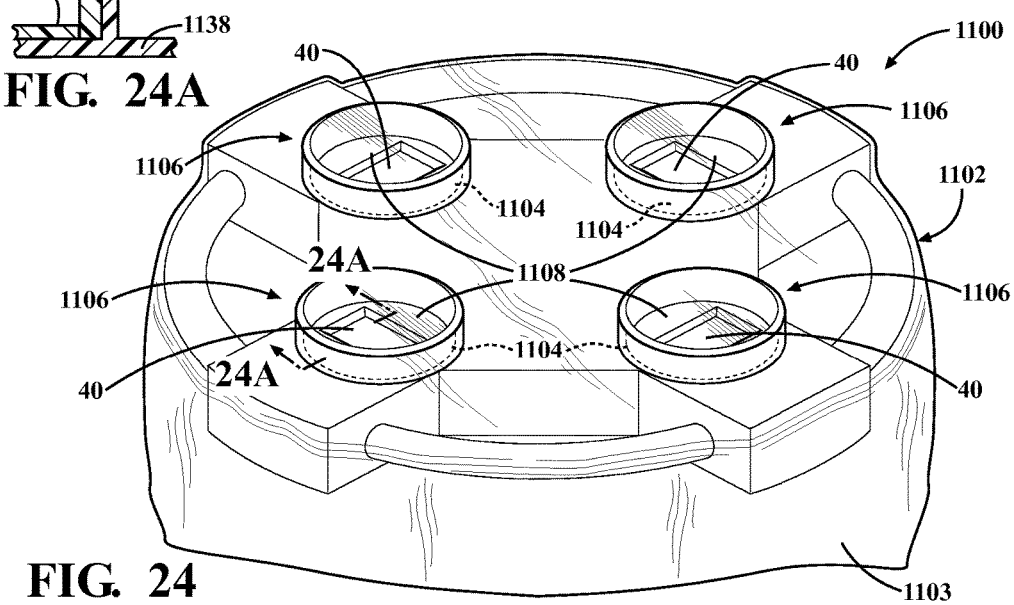
FIG. 24

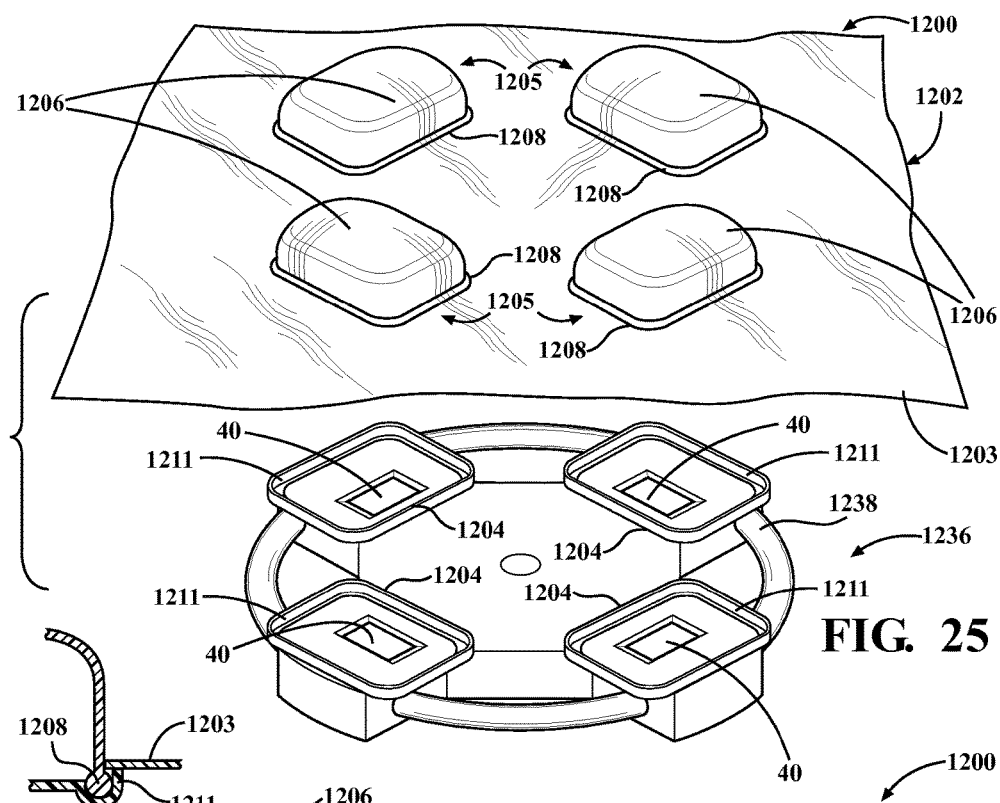
FIG. 25
FIG. 26A
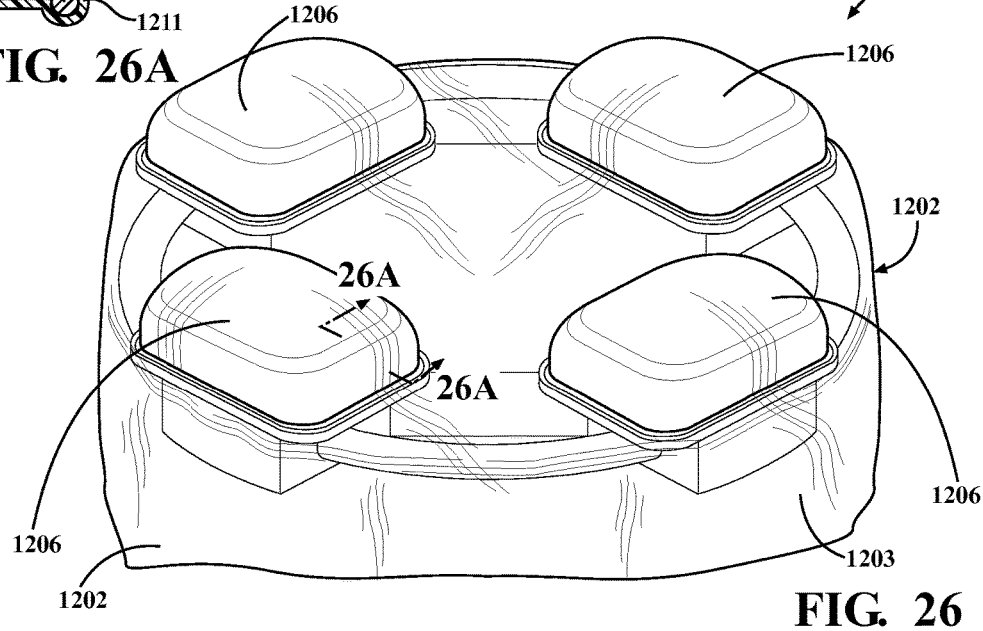
FIG. 26

ASSEMBLY FOR POSITIONING A STERILE SURGICAL DRAPE RELATIVE TO OPTICAL POSITION SENSORS

RELATED APPLICATIONS

This application claims priority to and all the benefits of U.S. Provisional Patent Application No. 61/788,752 which was filed on Mar. 15, 2013, which is hereby incorporated by reference in its entirety.

TECHNICAL FIELD

The present invention generally relates to a camera and drape assembly for an operating room. Specifically, the camera and drape assembly includes a camera unit having an optical sensor and a surgical drape for separating the camera unit from a sterile field of the operating room.

BACKGROUND

A sterile drape is used in some operating rooms to separate a sterile field for a surgical procedure. For example, some operating rooms include a guidance station that tracks movement of various objects in the operating room. Such objects include, for example, a surgical instrument and anatomy of the patient. The guidance station tracks these objects for purposes of displaying their relative positions and orientations to the surgeon and, in some cases, for purposes of controlling or constraining movement of the surgical instrument relative to a predefined path or anatomical boundary. Many components of the guidance station cannot be adequately and/or easily sterilized. As such, a sterile drape is used to separate at least some of the components of the guidance station from the sterile field.

The guidance station includes a localizer that includes a camera unit. The camera unit includes optical sensors, e.g., charge-coupled devices (CCD), for tracking the objects in the operating room. Specifically, the camera unit tracks the position of tracking devices fixed to objects in the operating room such as surgical instruments and anatomy of the patient. The optical sensors of the localizer receive light signals emitted from the tracking devices, e.g., with the use of light emitting diodes (LEDs) fixed to the tracking devices. Based on the positions of the tracking devices, the guidance station calculates the position and/or orientation of the surgical instrument and the anatomy of the patient.

An unobstructed view is sought between the optical sensors of the camera unit and the tracking devices so that the optical sensors can accurately detect the light signals transmitted by the tracking devices. The tracking devices are in the sterile field on the surgical instruments and on the anatomy of the patient. The camera unit cannot be adequately and/or easily sterilized, so the sterile drape separates the camera unit from the sterile field of the operating room and, thus, separates the camera unit from the tracking devices.

The sterile drape can interfere with proper light detection by the camera unit. For example, wrinkles in the sterile drape between the optical sensors and the tracking devices interfere with the ability of the optical sensors to adequately detect the tracking devices. As another example, if the drape extends at a transverse plane relative to the optical sensors, i.e., is not co-planar with the optical sensors, the drape can distort the light detection of the camera unit. As such, there remains an opportunity to provide an adequate view between the optical sensors of the camera unit outside of the sterile field and the tracking devices inside the sterile field so that the optical sensors can accurately detect the tracking devices.

SUMMARY

One embodiment provides a camera and drape assembly for use with a tracking element of a surgical system. A camera unit includes a casing. The camera unit further includes an optical sensor supported by the casing for detecting the tracking element. A drape includes a first section having a first elasticity and a second section surrounded by the first section and having a second elasticity greater than the first elasticity. The casing presents a lip with the second section extending around and elastically engaging the lip for supporting the drape over the optical sensor.

One advantage of this embodiment is that the lip supports the drape and positions the drape relative to the optical sensor to provide an unobstructed view between the optical sensor and the tracking element so that the optical sensor can accurately detect the tracking element. For example, the camera unit positions the drape in front of the optical sensors free of wrinkles that could interfere with proper detection by the optical sensor. As another example, the camera unit positions the drape in front of the optical sensor in substantially coplanar position relative to the optical sensor. As such, the camera unit allows for unobstructed line-of-sight between the optical sensor and the tracking element.

In another embodiment a camera and drape assembly is provided for use with a tracking element of a surgical system. A camera unit includes a casing. The camera unit further includes an optical sensor supported by the casing for detecting the tracking element. A drape includes a flexible section and a window that is rigid relative to the flexible section. The window is surrounded by the flexible section. The camera unit includes a first coupling device. The drape includes a second coupling device that mates with the first coupling device to align the window with the optical sensor.

One advantage of this embodiment is that the relatively rigid window provides a wrinkle-free, transparent sterile barrier between the camera unit and the tracking element that enables light signals from the tracking element to be properly received by the optical sensor. Additionally, the coupling devices further provide appropriate positioning of the drape on the camera unit to maintain alignment between the window and the optical sensor.

In another embodiment a camera and drape assembly is provided for use with a tracking element of a surgical system. The camera unit includes a casing having a base and a post extending upwardly from the base. The camera unit further includes a plurality of optical sensors supported by the casing for detecting the tracking element. A drape has a flexible section for draping over the post of the casing to cover the casing and the optical sensors. A collar is sized for fitting over the post to trap the flexible section of the drape between the collar and the post.

One advantage of this embodiment is that the collar is able to place tension on the flexible section across the casing to remove wrinkles and provide a wrinkle-free, transparent sterile barrier between the camera unit and the tracking element that enables light signals from the tracking element to be properly received by the optical sensors.

In another embodiment a drape is provided for use with a camera unit having a casing, an optical sensor supported by the casing, and a lip. The drape comprises a first section having a first elasticity and a second section surrounded by the first section and having a second elasticity greater than the first elasticity. The second section is configured to extend around and elastically engaging the lip of the camera unit for supporting the drape over the optical sensor.

In yet another embodiment, a drape is provided for use with a camera unit having a casing, an optical sensor supported by the casing, and a first coupling device. The drape comprises a flexible section and a window that is rigid relative to the flexible section and surrounded by the flexible section. The drape includes a second coupling device configured to mate with the first coupling device to align the window over the optical sensor.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 11 is a partially exploded view of a fifth embodiment of the camera assembly including a camera unit and a drape;

FIG. 12 is a perspective view of the camera assembly of FIG. 11 with the drape assembled to the camera unit;

FIG. 12A is a partial cross-sectional view taken generally along line 12A in FIG. 12;

FIG. 21 is a partially exploded view of a tenth embodiment of the camera assembly including a camera unit and a drape;

FIG. 22 is a perspective view of the camera assembly of FIG. 21 with the drape assembled to the camera unit;

FIG. 22A is a partial cross-sectional view taken generally along line 22A in FIG. 22;

FIG. 23 is a partially exploded view of a eleventh embodiment of the camera assembly including a camera unit and a drape;

FIG. 24 is a perspective view of the camera assembly of FIG. 23 with the drape assembled to the camera unit;

FIG. 24A is a partial cross-sectional view taken generally along line 24A in FIG. 24;

FIG. 25 is a partially exploded view of a twelfth embodiment of the camera assembly including a camera unit and a drape;

FIG. 26 is a perspective view of the camera assembly of FIG. 25 with the drape assembled to the camera unit;

FIG. 26A is a partial cross-sectional view taken generally along line 26A in FIG. 26;

DETAILED DESCRIPTION

Figure 1:
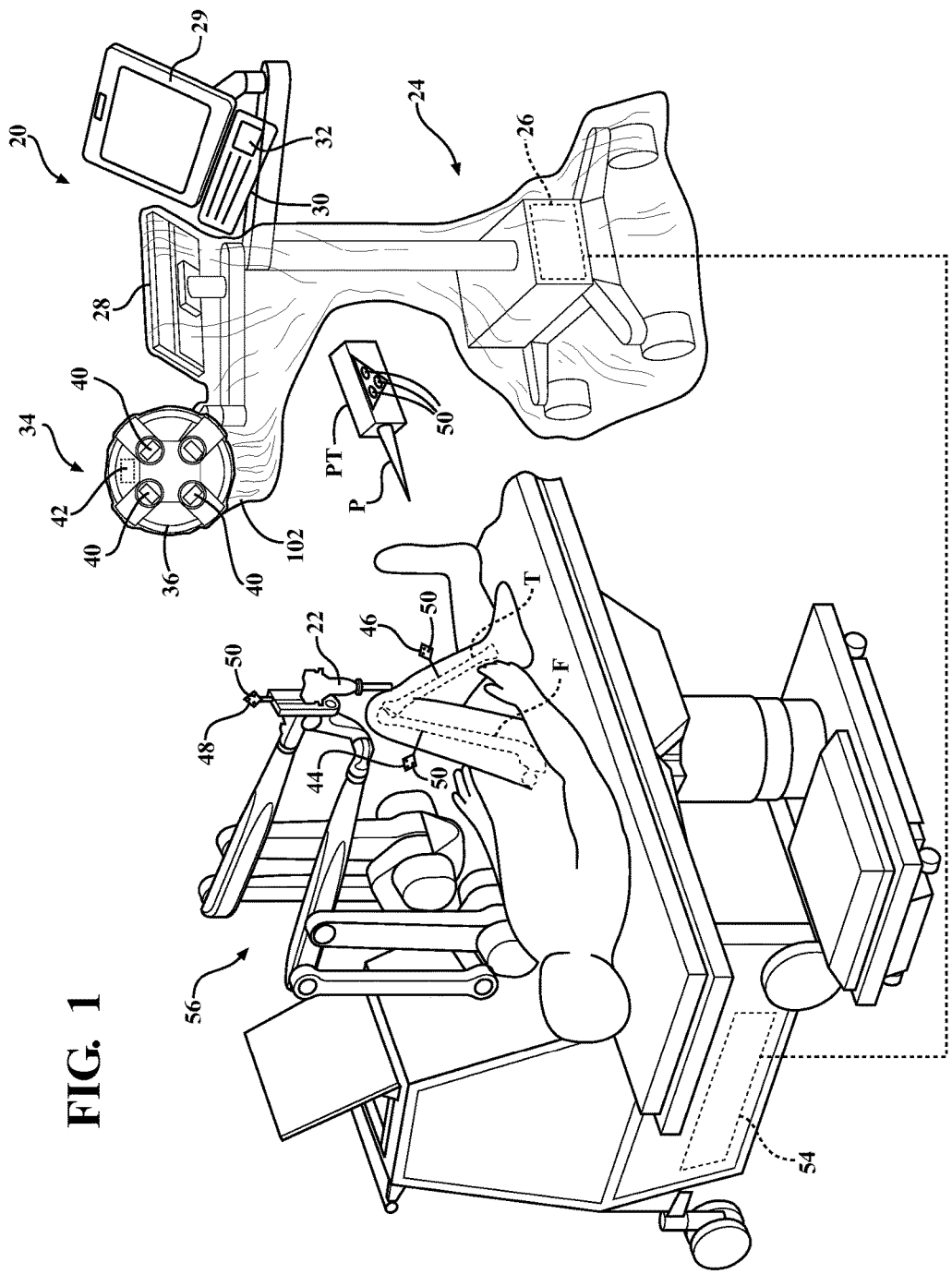
FIG. 1 is a perspective view of a guidance station including a camera assembly in an operating room.

With reference to FIG. 1, a surgical system includes a guidance station 20 and tracking devices associated with various objects. The tracking devices, e.g., trackers 44, 46, 48 discussed further below, are capable of communicating with the guidance station 20 to track the objects.

In FIG. 1, the guidance station 20 is shown in an operating room of a medical facility. A sterile drape, such as those described in the various embodiments below, separates a sterile field of the operating room. The guidance station 20 is set up to track movement of the various objects in the operating room. Such objects include, for example, a surgical instrument 22, a femur F, and a tibia T. The guidance station 20 tracks these objects for purposes of displaying their relative positions and orientations to the surgeon and, in some cases, for purposes of controlling or constraining movement of the surgical instrument 22 relative to a predefined path or anatomical boundary.

The guidance station 20 includes a computer cart assembly 24 that houses a navigation computer 26, or other type of control unit that includes one or more processors (not numbered). A navigation interface is in operative communication with the navigation computer 26. The navigation interface includes a first display 28 adapted to be situated outside of the sterile field and a second display 29 adapted to be situated inside the sterile field.

A camera assembly 34, also referred to as a localizer 34, communicates with the navigation computer 26. The camera assembly 34 tracks tracking elements of the surgical system. In the embodiment shown, the camera assembly 34 includes a camera unit 36, also referred to as a sensing device 36. The camera unit 36 also includes optical sensors 40 supported by the casing 38 and exposed through the casing 38 for detecting the tracking elements.

Figure 2:
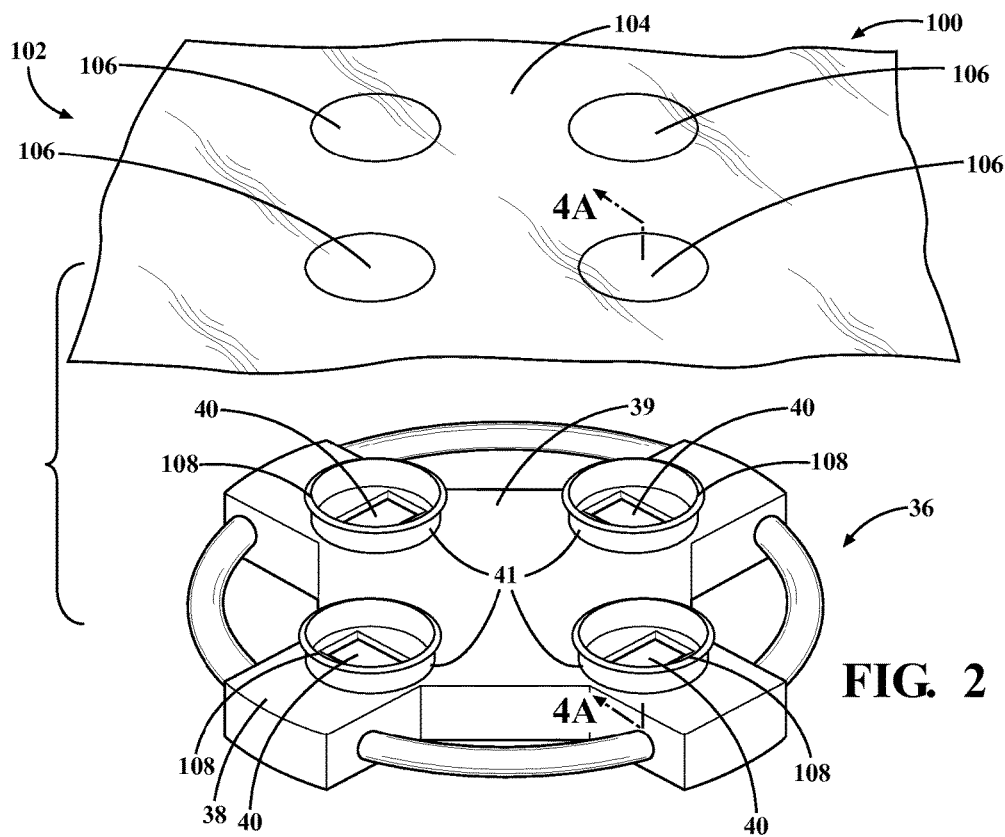
FIG. 2 is a partially exploded view of a first embodiment of the camera assembly including a camera unit and a drape.

Referring to FIG. 2, the camera unit 36 includes a casing 38 presenting a face 39 for facing the tracking elements, which in the disclosed embodiments are active or passive markers. Several embodiments of the casing are set forth below. In some embodiments at least two optical sensors 40 are employed. For example, as shown in several of the Figures, four optical sensors 40 are employed. The optical sensors 40 may be separate charge-coupled devices (CCD). It should be appreciated that in other embodiments, separate camera units, each with a separate CCD, or two or more CCDs, could also be arranged around the operating room. The optical sensors 40 detect infrared (IR) signals.

Camera unit 36 is mounted on an adjustable arm to position the optical sensors 40 with a field of view of the tracking elements that, ideally, is free from obstructions. The adjustable arm allows adjustment of the camera unit 36 in at least one degree of freedom and, in some embodiments, in two or more degrees of freedom.

With reference back to FIG. 1, the camera unit 36 includes a camera controller 42 (internal to casing 38) in communication with the optical sensors 40 to receive signals from the optical sensors 40. The camera controller 42 communicates with the navigation computer 26 through either a wired or wireless connection (not shown). Position and orientation signals and/or data are transmitted to the navigation computer 26 for purposes of tracking the objects. The displays 28, 29 and camera unit 36 may be like those described in U.S. Pat. No. 7,725,162 to Malackowski, et al. issued on May 25, 2010, entitled "Surgery System", hereby incorporated by reference.

Guidance station 20 communicates with the tracking elements on the tracking devices 44, 46, 48, also referred to herein as trackers. In the illustrated embodiment, one tracker 44 is firmly affixed to the femur F of the patient and another tracker 46 is firmly affixed to the tibia T of the patient. Trackers 44, 46 are firmly affixed to sections of bone. Trackers 44, 46 may be attached to the femur F and tibia T in the manner shown in U.S. Pat. No. 7,725,162, hereby incorporated by reference. Trackers 44, 46 could also be mounted like those shown in U.S. Provisional Patent Application No. 61/753,219, filed on Jan. 16, 2013, entitled, "Tracking Devices and Navigation Systems and Methods for Use Thereof", herein incorporated by reference. In additional embodiments, a tracker is attached to the patella (not shown) to track a position and orientation of the patella. In yet further embodiments, the trackers 44, 46 could be mounted to other tissue types or parts of the anatomy.

An instrument tracker 48 is rigidly attached to the surgical instrument 22. The instrument tracker 48 may be integrated into the surgical instrument 22 during manufacture or may be separately mounted to the surgical instrument 22 in preparation for the surgical procedure. The working end of the surgical instrument 22, which is being tracked by virtue of the instrument tracker 48, may be a rotating bur, electrical ablation device, or the like.

In the embodiment shown in FIG. 1, the surgical instrument 22 is an end effector of a machining station 56. Such an arrangement is shown in U.S. Provisional Patent Application No. 61/679,258, entitled, "Surgical Manipulator Capable of Controlling a Surgical Instrument in either a Semi-Autonomous Mode or a Manual, Boundary Constrained Mode", the disclosure of which is hereby incorporated by reference.

The optical sensors 40 of the camera assembly 34 receive light signals from the tracking elements of the trackers 44, 46, 48. In the illustrated embodiment, the trackers 44, 46, 48 are active trackers. In this embodiment, each tracker 44, 46, 48 has at least three active markers for transmitting light signals to the optical sensors 40. The active markers can be, for example, light emitting diodes or LEDs 50 transmitting light, such as infrared light. The optical sensors 40 preferably have sampling rates of 100 Hz or more, more preferably 300 Hz or more, and most preferably 500 Hz or more. In some embodiments, the optical sensors 40 have sampling rates of 8000 Hz. The sampling rate is the rate at which the optical sensors 40 receive light signals from sequentially fired LEDs 50. In some embodiments, the light signals from the LEDs 50 are fired at different rates for each tracker 44, 46, 48.

In other embodiments, the trackers 44, 46, 48 may have passive markers (not shown), such as reflectors that reflect and transmit light emitted from the camera unit 36. The reflected light is then received by the optical sensors 40. Tracking elements such as the above described active and passive markers are well known in the art.

Based on the positions of the LEDs 50 and previously loaded data relating to the patient's anatomy and the surgical instrument 22, navigation computer 26 determines the position and orientation of the surgical instrument 22 relative to the tissue (e.g., femur F and tibia T) against which the working end is to be applied. The previously loaded data includes data associated with pre-operative images, including MRI images, CT scans, etc. taken before the surgical procedure. The previously loaded data also includes geometric relationships between the working end of the surgical instrument 22 and the LEDs 50 on instrument tracker 48. Using navigation techniques for registration and coordinate system transformation, the patient's anatomy and the working end of the surgical instrument 22 can be registered into a coordinate reference frame of the localizer 34 so that the working end and the anatomy can be tracked together using the LEDs 50.

In some embodiments, navigation computer 26 forwards position and/or orientation data to a manipulator controller 54. The manipulator controller 54 can then use the data to control the machining station 56 as described in U.S. patent application Ser. No. 13/958,070, filed on Aug. 2, 2013, entitled, "Surgical Manipulator Capable of Controlling a Surgical Instrument in Multiple Modes," the disclosure of which is hereby incorporated by reference.

The navigation computer 26 also generates image signals that indicate the relative position of the surgical instrument working end to the surgical site. These image signals are applied to the displays 28, 29. Displays 28, 29, based on these signals, generate images that allow the surgeon and surgical personnel to view the relative position of the surgical instrument working end to the surgical site. The displays, 28, 29, as discussed above, may include a touch screen or other input/output device that allows entry of commands.

A sterile drape separates the guidance system 20 from the sterile field. The sterile drape is removeably engaged with the camera unit 36. The drape is typically formed of high-density polyethylene (HDPE) or low-density polyethylene (LDPE).

Several embodiments of camera and drape assemblies are set forth further below. If not properly arranged in front of the optical sensors 40, the drape can interfere with proper light detection by the optical sensors 40. For example, wrinkles in the drape in front of the optical sensors 40 or an offset inclination of the drape relative to the optical sensors 40 can interfere with proper light detection by the optical positioning sensors 40.

A first embodiment of a camera and drape assembly 100 is shown in FIGS. 2-4b. The assembly 100 includes a drape 102 and the camera unit 36. The drape 102 includes a first section 104 and a plurality of second sections 106 surrounded by the first section 104. The first section 104 has a first elasticity and the second sections 106 each have a second elasticity greater than the first elasticity, making the second sections 106 more elastic than the first section 104 and capable of greater stretching than the first section 104.

Figure 4A:
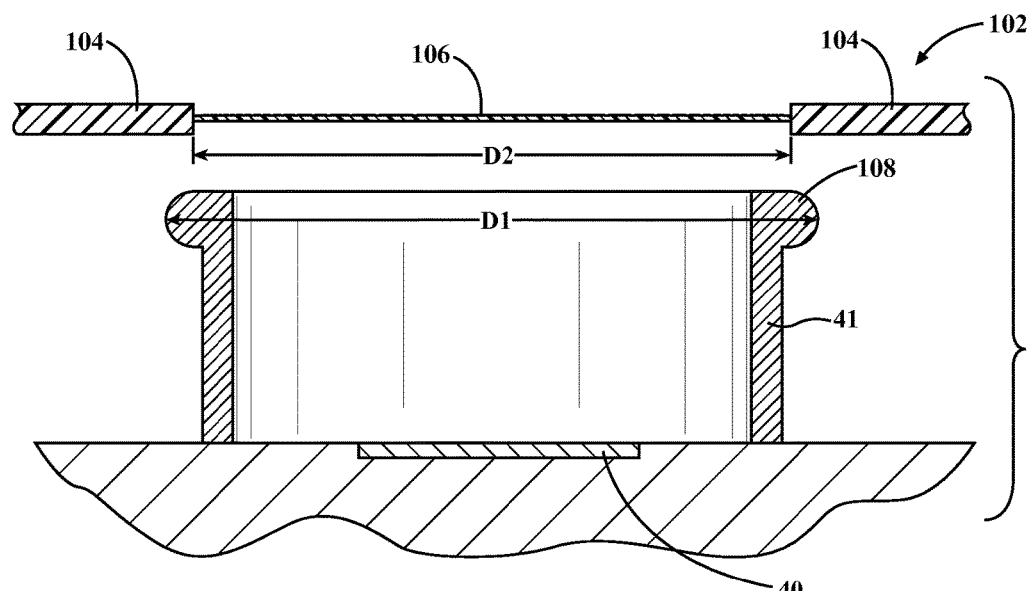
FIG. 4A is a cross-section view of a portion of the camera assembly taken along line 4A of FIG. 2.

With reference to FIG. 4a, the second sections 106 are thin relative to the first section 104. In such a configuration, the second sections 106 can be formed of the same material as the first section 104 and the relative thickness of the second sections 106 provides the second sections 106 with the second elasticity greater than the first elasticity. Alternatively, the first section 104 can be formed of a first material and the second sections 106 can be formed of a second material different than the first material and having greater elasticity than the first material. In such a configuration, the thickness of the second sections 106 can be similar to or different than the thickness of the first section 104.

As one example, the drape 102 may contain two or more second sections 106 with each second section 106 being surrounded by the first section 104. As shown in FIG. 2, the drape 102 includes four second sections 106. Specifically, the drape 102 includes one second section 106 associated with each optical sensor 40 and each second section 106 is disposed between the optical sensor 40 and at least one of the trackers 44, 46, 48.

The second sections 106 are integrated with the first section 104, i.e. the first section 104 and the second sections 106 are a one-piece unit. For example, the first section 104 and the second sections 106 can be formed together simultaneously as a unit or can be formed separately and subsequently assembled and fixed together. The second sections 106 are clear or transparent to allow light to pass through without obstruction. The second sections 106 are shown circular in shape, but other shapes are contemplated.

Figure 3:
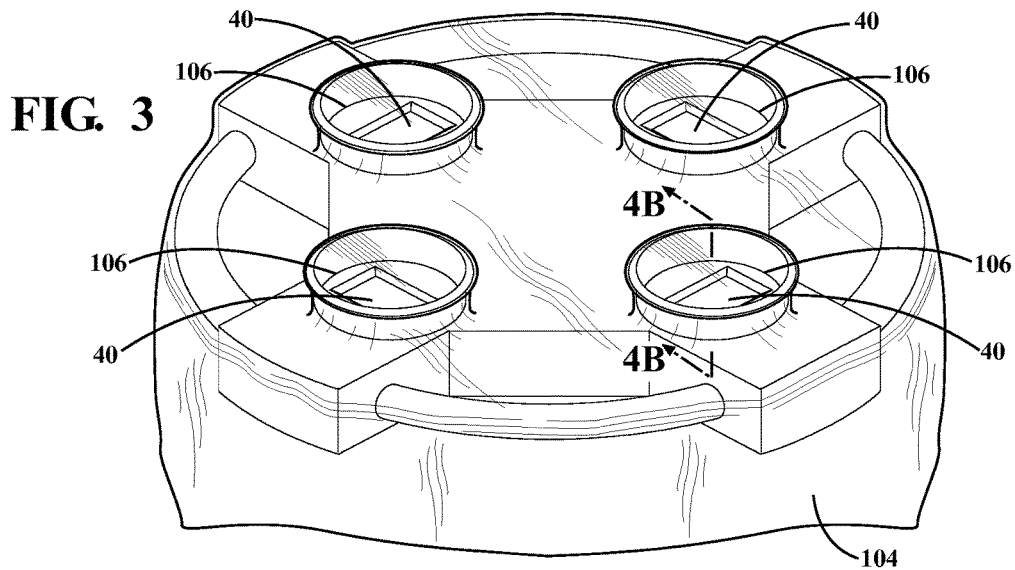
FIG. 3 is a perspective view of the camera assembly of FIG. 2 with the drape assembled to the camera unit.

With reference to FIGS. 2-4B, the camera unit 36 includes a lip 108 spaced from the face 39 of the casing 38. A support member 41 extends from the face 39 of the casing 38 to the lip 108. The support member 41 extends circumferentially about one of the optical position sensors 40. The lip 108 extends circumferentially about the support member 41. The lip 108 is annular, as shown in FIGS. 2 and 3. The support member 41 is also annular. However, the lip 108 and the support member 41 can be of any suitable shape without departing from the nature of this embodiment.

The camera unit 36 includes a plurality of lips 108 and support members 41 with each lip 108 and support member 41 corresponding with one optical sensor 40. In other words, the camera unit 36 may include two or more lips 108.

Figure 4B:
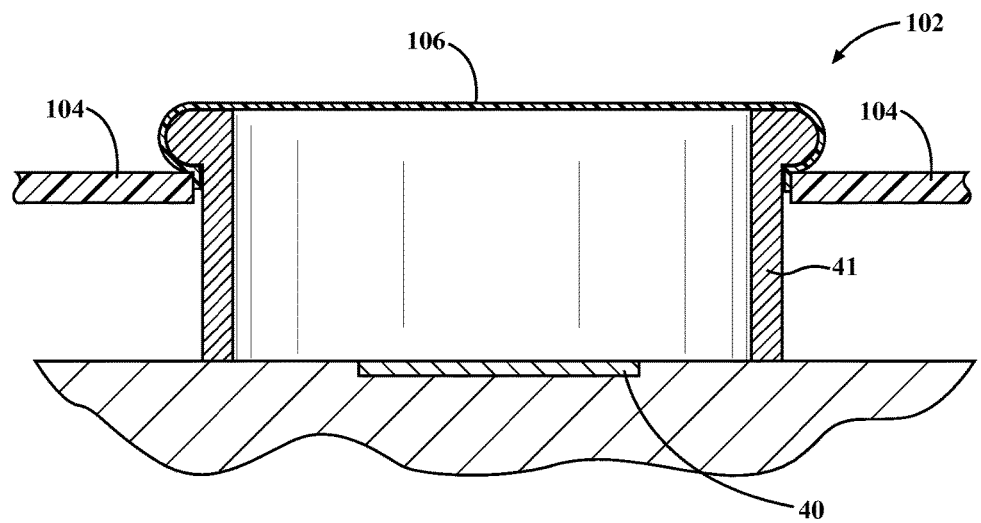
FIG. 4B is a cross-section view of a portion of the camera assembly taken along line 4B of FIG. 3.

With reference to FIGS. 4A-B, each of the second sections 106 align with one of the lips 108, as shown in FIG. 4A, and is stretched over the lip 108, as shown in FIG. 4B. When disassembled from each other, and with the second section 106 in its normal state, the lip 108 has a first diameter D1 and the second section 106 has a second diameter D2. The second diameter D2 is less than the first diameter D1 of the lip 108, as shown in FIG. 4A. In some cases, D2 is approximately the same diameter as an outer diameter of the support member 41.

The second section 106 is stretched over the lip 108 and retained on the lip 108, as shown in FIG. 4B. Retention is furthered by the first section 104 being stretchable over the lip 108, but having lesser elasticity and thereby constraining the second section 106 in position over the lip 108. The second section 106 is configured to stretch uniformly across the lip 108 such that wrinkles do not develop in the second section 106. For example, the annular shape of the lip 108 shown in FIGS. 2 and 3 encourage uniform stretching. The drape 102 is removed from the camera unit 36 by pulling the drape 102 to separate the second sections 106 from the lips 108.

The engagement of the second sections 106 on the lip 108 provides visual confirmation that the drape 102 is properly positioned relative to the camera unit 36 and associated optical sensors 40. Specifically, the visual difference in thickness of the second sections 106 in comparison to the first section 104 indicates proper positioning of the second sections 106 relative to the camera unit 36.

The drape 102 can also include visual indicator elements 109 to aid in alignment of the stretchable second sections 106 relative to the camera unit 36. For example, the visual indicator elements 109 can be colored rings that encircle the second sections 106. The colored rings, such as rings of colored ink applied to the drape 102 could be located either at the boundary between the first section 104 and the second sections 106 or close thereto.

Figure 5:
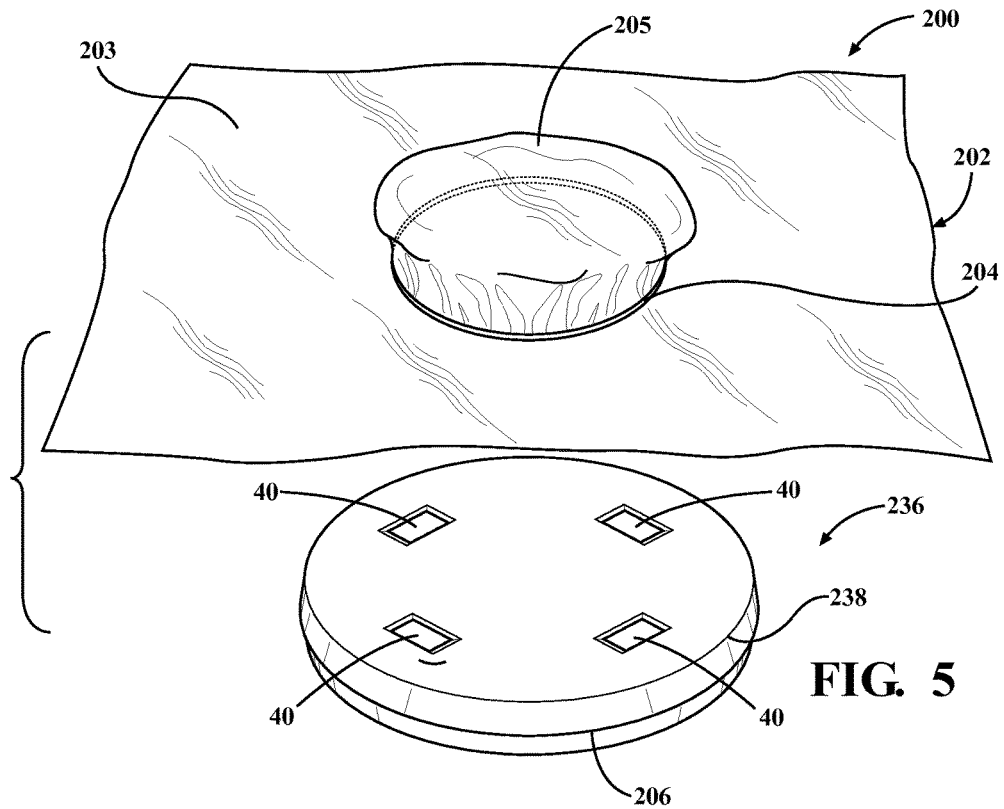
FIG. 5 is a partially exploded view of a second embodiment of the camera assembly including a camera unit and a drape.
Figure 6:
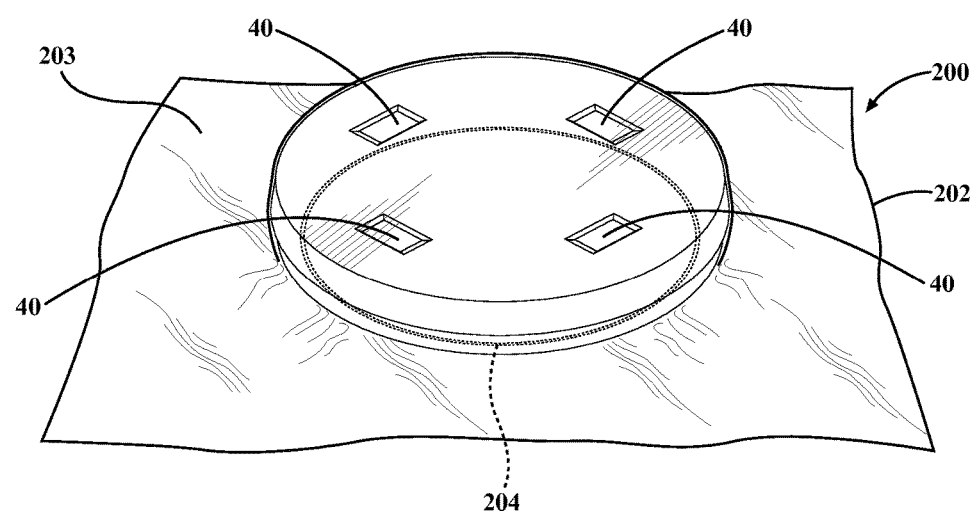
FIG. 6 is a perspective view of the camera assembly of FIG. 5 with the drape assembled to the camera unit.

With reference to FIGS. 5 and 6, a second embodiment of a camera and drape assembly 200 positions a drape 202 on a casing 238 of the camera unit 236. The drape 202 includes a first flexible section 203 and a second flexible section 205 surrounded by the first section 203. In one version, the first section 203 has a first elasticity and the second section 205 has a second elasticity greater than the first elasticity, making the second section 205 more elastic than the first section 203 and capable of greater stretching than the first section 203. In the version shown, the first and second sections 203, 205 have the same elasticity.

An elastic band 204 is attached to the first section 203 about the second section 205 to position the drape 202 on the camera unit 236 and to retain the drape 202 on the camera unit 236. Specifically, the outer casing 238 of the camera unit 236 defines a lip 206 extending circumferentially about the camera unit 236 and the elastic band 204 is configured to elastically hold the second section 205 when stretched over the lip 206. The elastic band 204 can be attached to the first section 203 in any fashion, such as, for example, adhesive, bonding, etc. In this embodiment, the lip 206 and elastic band 204 act as first and second coupling devices for coupling the drape 202 to the camera unit 236.

The first and second sections 203, 205 of the drape 202 are formed of thin, highly flexible, transparent film or foil such as polyethylene (PE) film. The first section 203 has a constant transparency and thickness. The second section 205 has a constant transparency and thickness. The second section 205 may be thinner than the first section 203 to make the second section 205 more elastic or may be of generally the same thickness. Alternatively, the second section 205 could include portions of different transparency and thickness than the first section 203, e.g., relatively clear and thin, in an area that covers the camera unit 236.

The engagement of the elastic band 204 on the lip 206 provides visual confirmation that the drape 202 is properly positioned relative to the camera unit 236. The engagement of the elastic band 204 on the lip 206 can smooth the second section 205 of the drape 202 across the casing 238 and/or stretches the second section 205 of the drape 202 across the casing 238, which can thin the drape 202 in the area in front of the optical position sensors 40 and reduce potential interference with proper light detection by the optical position sensors 40.

Figure 7:
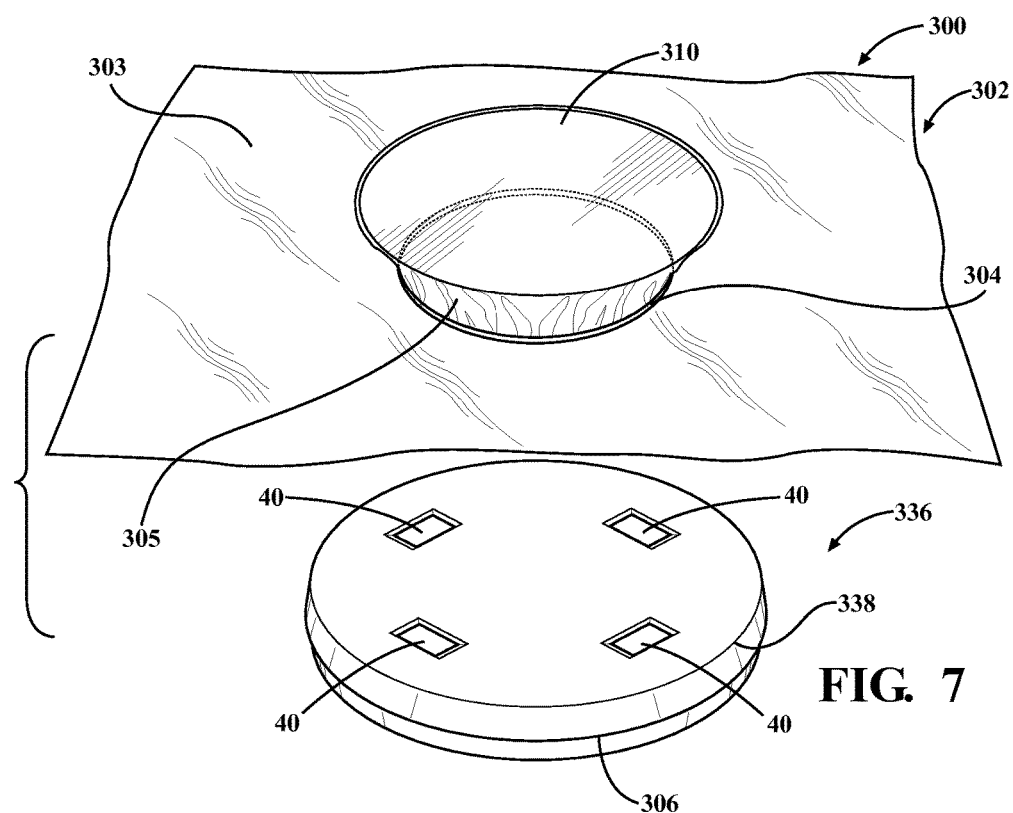
FIG. 7 is a partially exploded view of a third embodiment of the camera assembly including a camera unit and a drape.
Figure 8:
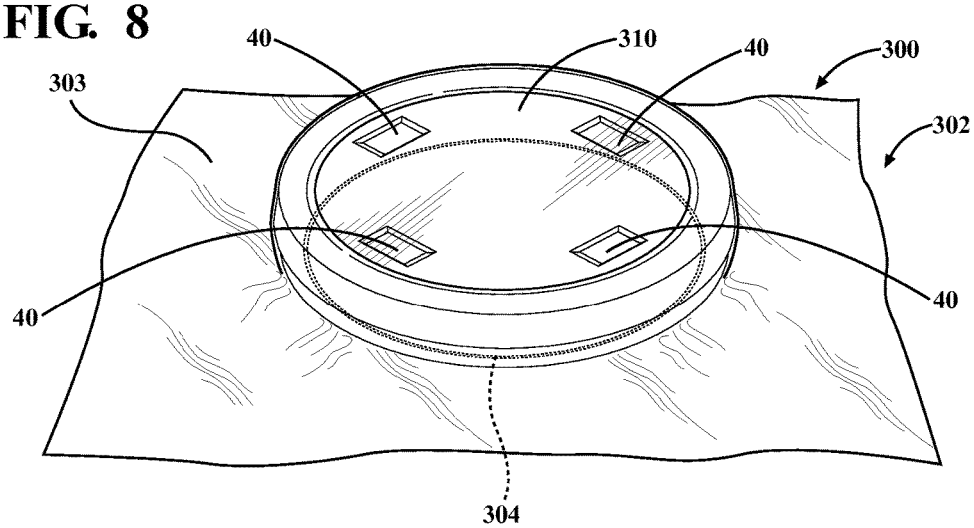
FIG. 8 is a perspective view of the camera assembly of FIG. 7 with the drape assembled to the camera unit.

With reference to FIGS. 7 and 8, a third embodiment of a camera and drape assembly 300 positions a drape 302 on an outer casing 338 of the camera unit 336. The drape 302 includes a first flexible section 303 and a second flexible section 305 surrounded by the first section 303. In one version, the first section 303 has a first elasticity and the second section 305 has a second elasticity greater than the first elasticity, making the second section 305 more elastic than the first section 303 and capable of greater stretching than the first section 303. In the version shown, the first and second sections 303, 305 have the same elasticity.

The drape 302 also includes a rigid section 310. The rigid section 310 provides a window through which light emitted by the tracking elements can be received by the optical sensors 40.

An elastic band 304 is attached to the first section 303 to position the drape 302 on the camera unit 336. Specifically, the outer casing 338 of the camera unit 336 defines a lip 306 extending circumferentially about the camera unit 336 and the elastic band 304 is configured to elastically engage the lip 306. In this embodiment, the lip 306 and elastic band 304 act as first and second coupling devices for coupling the drape 302 to the camera unit 336.

The second section 305 separates the elastic band 304 from the rigid section 310. When attached to the camera unit 336, the rigid section 310 is located in front of the optical position sensors 40. In one embodiment, the elastic band 304 has a diameter that, in its normal state, is less than a diameter of the rigid section 310 (see FIG. 7) thereby requiring the elastic band 304 to be stretched over the casing 338.

The rigid section 310 covers the optical position sensors 40 when the elastic band 304 is engaged with the lip 306. In some cases the elastic band 304 is stretched over the entire casing 338, including the lip 306, and allowed to at least partially relax adjacent a back surface of the casing 338. The first section 303 is also stretchable in order to enable the elastic band 304 to stretch over the casing 338. The rigid section 310 typically abuts the casing 338 when the elastic band 304 is engaged with the lip 306.

The engagement of the elastic band 304 on the lip 306 and the placement of the rigid section 310 in front of the optical position sensors 40 provide visual confirmation that the drape 202 is properly positioned relative to the camera unit 336.

The first and second sections 303, 305 are formed of thin, highly flexible, transparent film or foil, such as polyethylene film. The rigid section 310 is formed of a plastic sheet that is rigid relative to the first and second sections 303, 305 and is transparent. The second section 305 defines a cutout that receives the rigid section 310. The rigid section 310 is fixed to the second section 305 in the cutout by, for example, bonding, adhesive, tape, etc.

Figure 9:
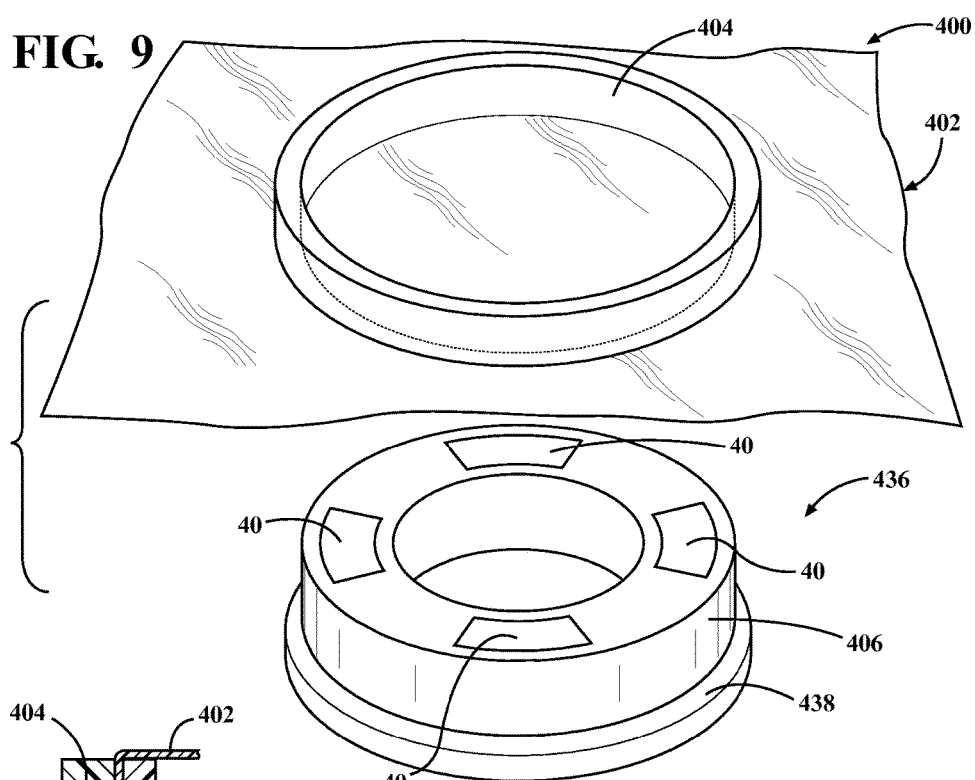
FIG. 9 is a partially exploded view of a fourth embodiment of the camera assembly including a camera unit and a drape.
Figure 10A:
FIG. 10A is a partial cross-sectional view taken generally along line 10A in FIG. 10.
Figure 10:
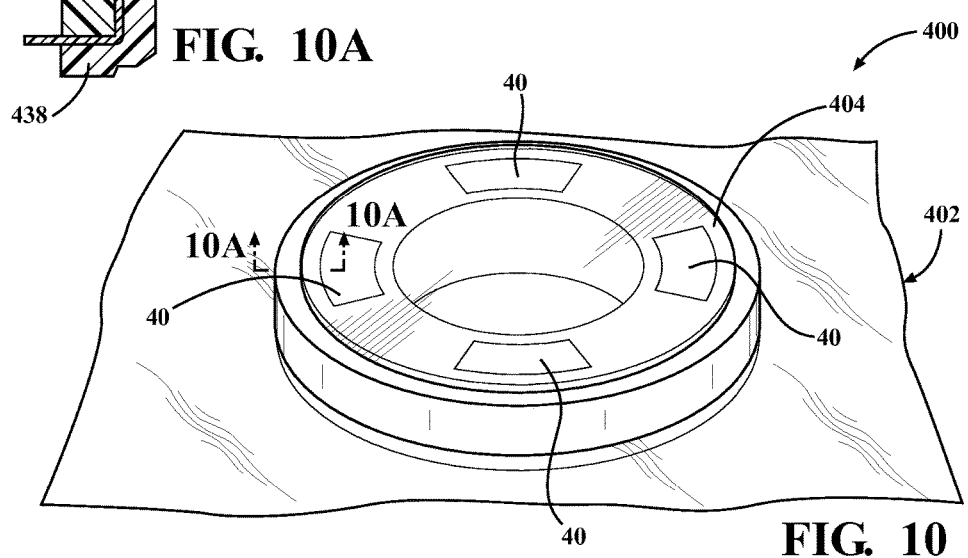
FIG. 10 is a perspective view of the camera assembly of FIG. 9 with the drape assembled to the camera unit.

With reference to FIGS. 9, 10, and 10A, a fourth embodiment of a camera and drape assembly 400 positions a drape 402 on an outer casing 438 of the camera unit 436. A rigid collar 404 clamps the drape 402 in position relative to the camera unit 436. Specifically, a post 406 extends from a base of the outer casing 438 of the camera unit 436. The post 406 supports the optical position sensors 40. The collar 404 is configured to engage about the post 406 and pinch the drape 402 between the collar 404 and the post 406. The collar 404 is separate from and moveable relative to drape 402. The collar 404 may have rounded edges to prevent tearing of the drape 402.

The post 406 defines an outer diameter and the collar 404 defines an inner diameter configured to receive the outer diameter of the post 406. The collar 404 is initially placed on the post 406 with the drape 402 disposed therebetween, as shown in FIG. 10A, and is pressed onto the post 406 toward the base of the outer casing 438 to stretch the drape 402 across the optical position sensors 40. The collar 404 is retained on the post 406 by a friction fit and by resting on the base. Alternatively, the collar 404 and the post 406 include engagement features (not shown) for retaining the collar 404 on the post 406.

The drape 402 is formed of highly flexible, transparent film or foil such as polyethylene film. The drape 402 has a constant transparency and thickness. Alternatively, the drape 402 includes sections of different transparency and thickness, e.g., relatively clear and thin, in an area that covers the camera unit 436. The collar 404 and the post 406, for example, are formed of plastic or metal.

The engagement of the collar 404 on the post 406 provides visual and tactile confirmation that the drape 402 is properly positioned relative to the camera unit 436. The collar 404 and/or the post 406 can include features that provide acoustic feedback when the collar 404 is engaged with the post 406, such as snap-lock engagement features.

With reference to FIGS. 11, 12, and 12A, a fifth embodiment of a camera and drape assembly 500 positions a drape 502 on the outer casing 538 of the camera unit 536. The camera unit 536 includes first coupling devices 504 fixed to and extending from the casing 538 peripherally about the optical position sensors 40. The first coupling devices 504 are generally rectangular and include a first peripheral wall 505 extending upwardly from the casing 538.

The drape 502 includes a flexible section 503 and windows 508 coupled to the flexible section 503 through which the optical sensors 40 are able to receive light signals from the tracking elements.

The drape 502 further includes second coupling devices 506 configured to engage the first coupling devices 504. The second coupling devices may be generally rectangular in shape. Specifically, the first coupling devices 504 and the second coupling devices 506 are configured to engage each other in a friction fit or snap-fit connection.

The second coupling devices 506 each include a second peripheral wall 511 that extends from the drape 502 to the window 508. The window 508 is a transparent planar section fixed to the second peripheral wall 511 that is aligned with the optical position sensors 40 when the second coupling devices 506 are engaged with the first coupling devices 504. The windows 508 may be integrally formed with the second peripheral wall 511 or may be separate (as shown) and fixed to the second peripheral wall 511 by adhesive, bonding, ultrasonic welding, or other methods.

The engagement of the second coupling devices 506 with the first coupling devices 504 positions the drape 502 relative to the camera unit 536 and supports the drape 502 on the camera unit 536. When engaged the peripheral walls 505, 511 abut one another with the second peripheral wall 511 surrounding the first peripheral wall 505. The peripheral walls 505, 511 although rigid relative to the flexible section 503 may be flexible to facilitate a friction fit therebetween. Snap-fit features may also be integrated into either of the peripheral walls 505, 511 to facilitate engagement.

The flexible section 503 of the drape 502 is formed of highly flexible, transparent film or foil such as polyethylene film. The second coupling devices 506 and windows 508 are typically formed of a plastic that is rigid relative to the flexible section 502. The windows 508 are transparent. The flexible section 503 defines cutouts that receive the second coupling devices 506. The second coupling devices 506 are fixed to the flexible section 503 in the cutouts by, for example, bonding, adhesive, tape, etc.

The engagement of the second coupling devices 506 with the first coupling devices 504 provides tactile confirmation that the drape 502 is properly positioned relative to the camera unit 536. The second coupling devices 506 may include colored borders 510 to identify the portion of the second coupling devices 506 that engage the first coupling devices 504.

Figure 13:
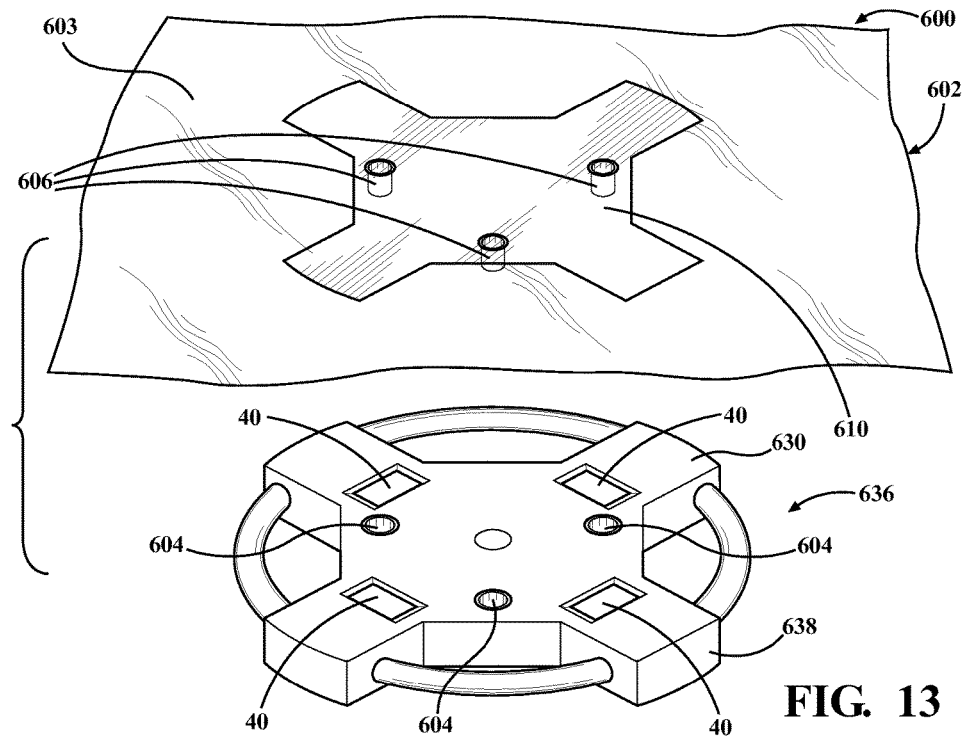
FIG. 13 is a partially exploded view of a sixth embodiment of the camera assembly including a camera unit and a drape.
Figure 14:
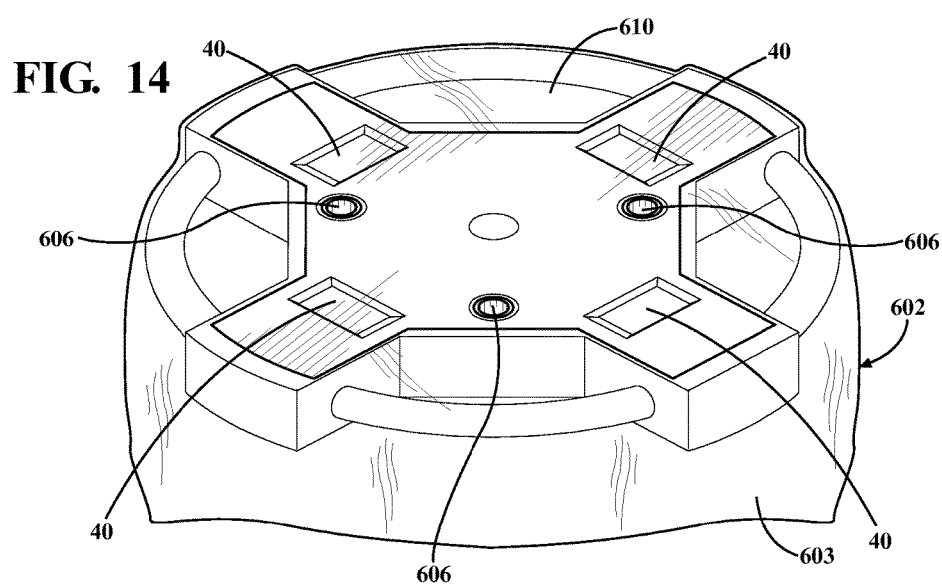
FIG. 14 is a perspective view of the camera assembly of FIG. 13 with the drape assembled to the camera unit.

With reference to FIGS. 13 and 14, a sixth embodiment of a camera and drape assembly 600 positions a drape 602 on an outer casing 638 of the camera unit 636. The drape 602 includes a flexible section 603, i.e. a first section 603, and a rigid section 610, i.e. a second section 610. The rigid section 610 is surrounded by the flexible section 603. The rigid section 610 provides a window through which light emitted by the tracking elements can be received by the optical sensors 40.

The outer casing 638 includes first coupling devices 604. In the embodiment shown the first coupling devices 604 are sockets 604. The drape 602 includes second coupling devices 606 for releasably coupling to the first coupling devices 604. The second coupling devices 606 are shown as plugs 606 coupled to the drape 602. The plugs 606 are configured to releasably fit in the sockets 604 to mount and position the drape 602 on the camera unit 636.

The plugs 606 are fixed to the rigid section 610, such as by adhesive, bonding, ultrasonic welding, or other methods. The rigid section 610 covers the optical position sensors 40 when the plugs 606 engage and mate with the sockets 604. In FIG. 13, the plugs 606 are located beneath the flexible section 603, but are visible in FIG. 13 since the flexible section 603 is transparent. In some embodiments, two, three, or more plugs 606 are employed to prevent rotation of the drape 602 relative to the casing 638. In other embodiments, a single plug having a non-circular geometry may be employed to prevent rotation of the drape 602 relative to the casing 638.

The flexible section 603 is formed of highly flexible, transparent film or foil such as polyethylene film. The rigid section 610 is formed of a plastic sheet that is rigid relative to the flexible section 603 and is transparent. The flexible section 603 defines a cutout that receives the rigid section 610. The rigid section 610 is fixed to the flexible section 603 in the cutout by, for example, bonding, adhesive, tape, etc.

The coupling of the plugs 606 and sockets 604 provides visual and tactile confirmation that the drape 602 is properly positioned relative to the camera unit 636.

Figure 15:
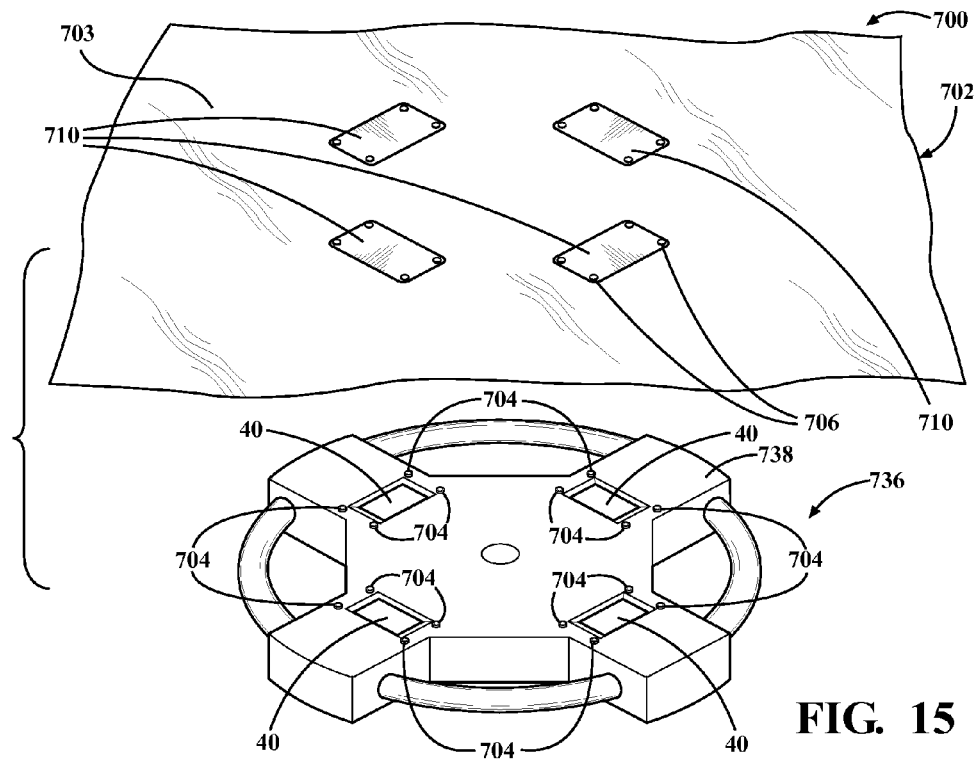
FIG. 15 is a partially exploded view of a seventh embodiment of the camera assembly including a camera unit and a drape.
Figure 16:
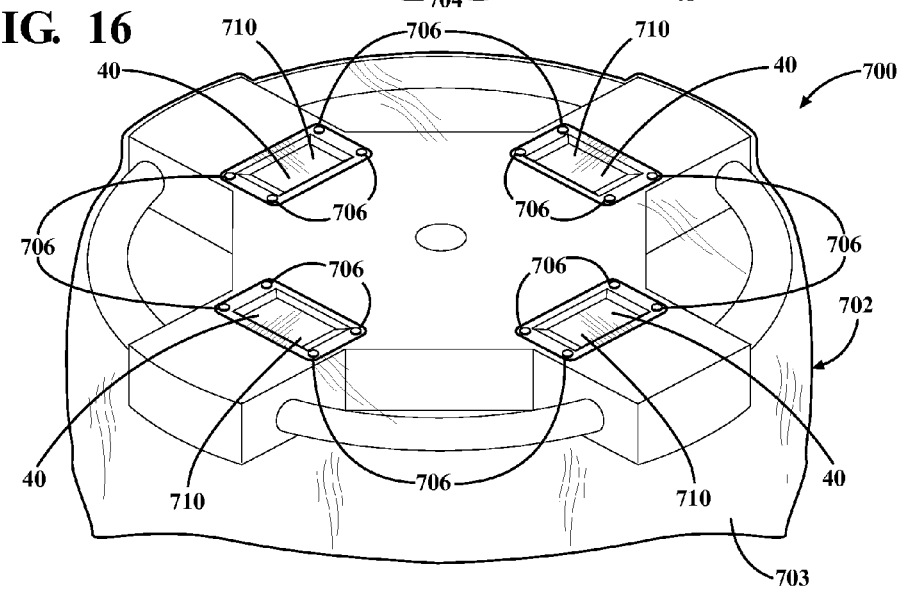
FIG. 16 is a perspective view of the camera assembly of FIG. 15 with the drape assembled to the camera unit.

With reference to FIGS. 15 and 16, a seventh embodiment of a camera and drape assembly 700 positions a drape 702 on a casing 738 of the camera unit 736. The drape 702 includes a flexible section 703, i.e., a first section 703, and rigid sections 710, i.e., second sections 710. The rigid sections 710 provide windows through which light emitted by the tracking elements can be received by the optical sensors 40.

First coupling devices 704 are fixed to the outer casing 738. The drape 702 includes second coupling devices 706 for coupling to the first coupling devices 704. In this embodiment, the first and second coupling devices 704, 706 are male and female parts or portions 704, 706 of conventional snap fasteners (the male parts could be on the drape 702 with the female parts on the camera unit 736 or vice versa). The snap portions 704, 706 are configured to releasably couple to each other to mount and position the drape 702 on the camera unit 736 and to support the drape 702 on the camera unit 736.

The rigid sections 710 cover the optical position sensors 40 when the snap portions 704, 706 couple to each other. The second snap portions 706 are fixed to the rigid section 710 of the drape 702. The first snap portions 704 are mounted and fixed to the casing 738 about the optical sensors 40.

The flexible section 703 is formed of highly flexible, transparent film or foil such as polyethylene film. The rigid section 710 is formed of a plastic sheet that is rigid relative to the flexible section 703 and is transparent. The flexible section 703 defines a plurality of cutouts that receive the rigid sections 710. The rigid sections 710 are fixed to the flexible section 703 in the cutout by, for example, bonding, adhesive, tape, etc.

The engagement of the first and second coupling devices 704, 706 provides acoustic and tactile confirmation that the drape 702 is properly positioned relative to the camera unit 736, e.g., by snapping.

Figures 17, 18A:
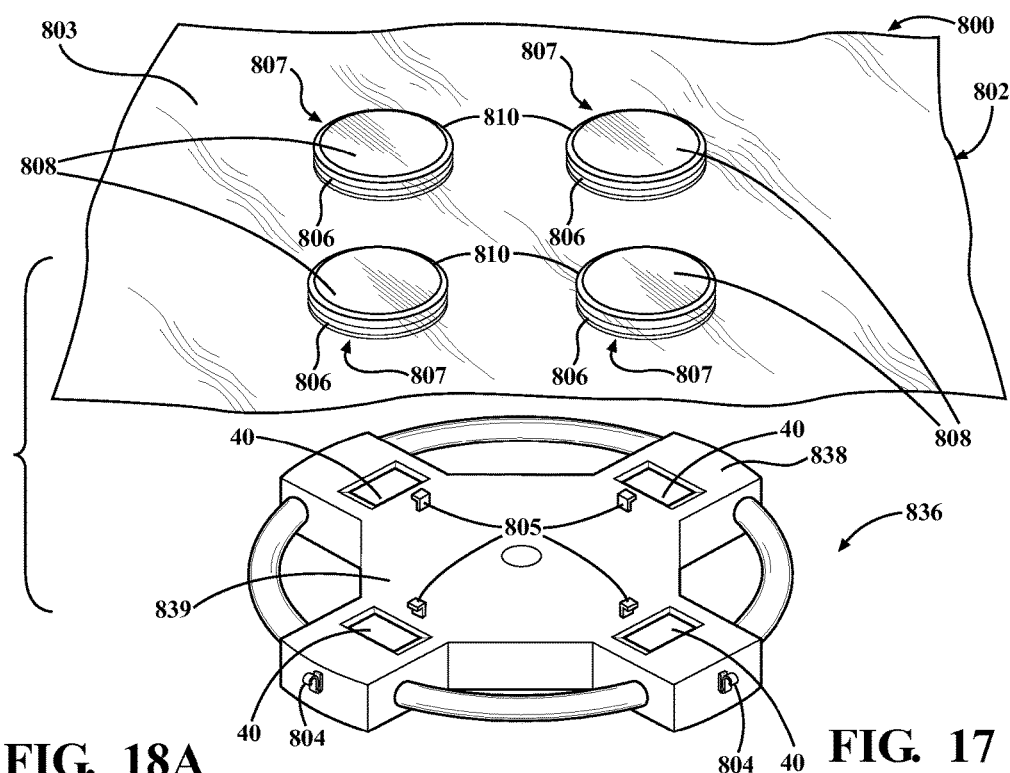
FIG. 17 is a partially exploded view of a eighth embodiment of the camera assembly including a camera unit and a drape.
FIG. 18A is a partial cross-sectional view illustrating an abutment and elastic band.
Figure 18:
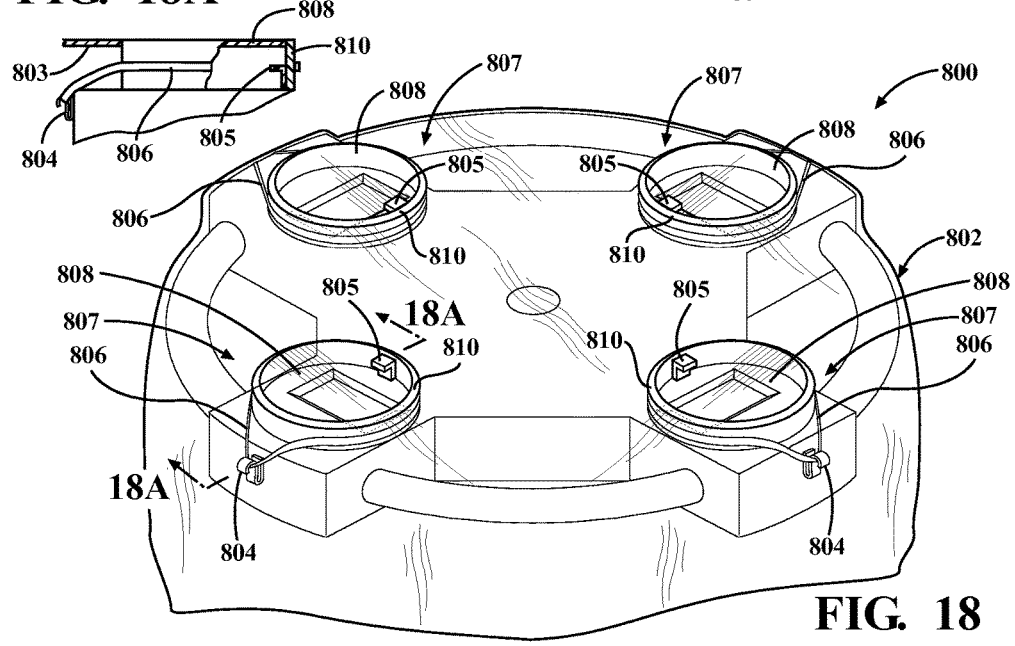
FIG. 18 is a perspective view of the camera assembly of FIG. 17 with the drape assembled to the camera unit.

With reference to FIGS. 17, 18, and 18A, an eighth embodiment of a camera and drape assembly 800 positions a drape 802 on an outer casing 838 of the camera unit 836. The drape 802 includes a flexible section 803, i.e., a first section 803, and rigid sections 807, i.e., second sections 807. The rigid sections 807 provide windows 808 through which light emitted by the tracking elements can be received by the optical sensors 40. The rigid sections 807 are spaced from one another and separated by the flexible section 803.

The rigid sections 807 are fixed to the flexible section 803. The rigid sections 807, also referred to as covers or caps, each have an upper planar wall forming the window 808 and a peripheral wall 810. The windows 808 may be integrally formed with the peripheral walls 810 or may be separate and fixed to the peripheral walls 810 by adhesive, bonding, ultrasonic welding, or other methods. The peripheral wall 810 is fixed to the flexible section 803. The windows 808 are parallel with a face 839 of the casing 838.

The camera unit 836 includes first coupling devices 804. In this embodiment, the first coupling devices 804 are retainers in the form of clips 804 fixed to and extending from the outer casing 838. The drape 802 includes a plurality of second coupling devices 806 for coupling to the clips 804. In this embodiment, the second coupling devices 806 are flexible, elastic bands 806 configured to engage the clips 804 to position the drape 802 relative to the camera unit 836 and to support the drape 802 on the camera unit 836.

Abutments 805, also known as stops or positioning elements, are configured to be received inside the peripheral wall 810 of the rigid sections 807 to hold the windows 808 in place as the elastic bands 806 bias the rigid sections 807 against the abutments 805. The elastic bands 806 encircle the peripheral walls 810 around substantially the perimeter of the peripheral walls 810 and are attached to the clips 804 while under tension as a result of the abutments 805 holding the rigid sections 807 in place.

The windows 808 cover the optical position sensors 40 when the elastic bands 806 are coupled to the clips 804. The peripheral walls 810 abut the casing 838 when the elastic bands 806 are coupled to the clips 804. The rigid sections 807 may be fixed to the flexible section 803 such that the peripheral walls 810 extend below the flexible section 803, as shown. In this case, the elastic bands 806 engage the clips 804 beneath the flexible section 803.

In other embodiments, the rigid sections 807 are fixed to the flexible section 803 such that the peripheral walls 810 extend above the flexible section 803. In this case, the elastic bands 806 engage the clips 804 through the flexible section 803. In either case, the rigid sections 807 are sized to fit over the optical position sensors 40 with the abutments 805 being received within the rigid sections 807.

The engagement of the elastic bands 806 with the clips 804 provides visual and tactile confirmation that the drape 802 is properly positioned relative to the camera unit 836. Additionally, the abutments 805 provide a tactile indication that the rigid sections 807 are abutting the abutments 805.

The flexible section 803 of the drape 802 is formed of highly flexible, transparent film or foil such as polyethylene film. The rigid sections 807 are formed of a plastic that is rigid relative to the flexible section 803. The rigid sections 807 may be entirely transparent or only the windows 808 may be transparent. The flexible section 803 defines cutouts that receive the rigid sections 807. The rigid sections 807 are fixed to the flexible section 803 in the cutout by, for example, bonding, adhesive, tape, etc.

Figure 19:
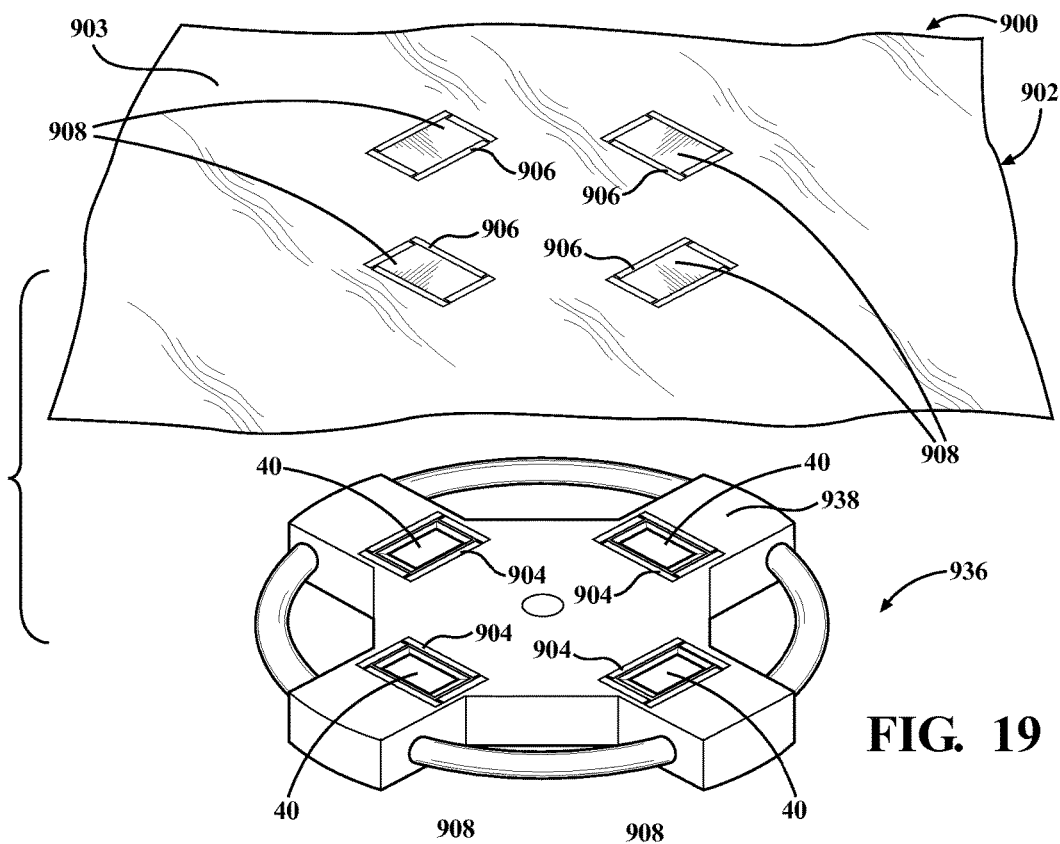
FIG. 19 is a partially exploded view of a ninth embodiment of the camera assembly including a camera unit and a drape.
Figure 20:
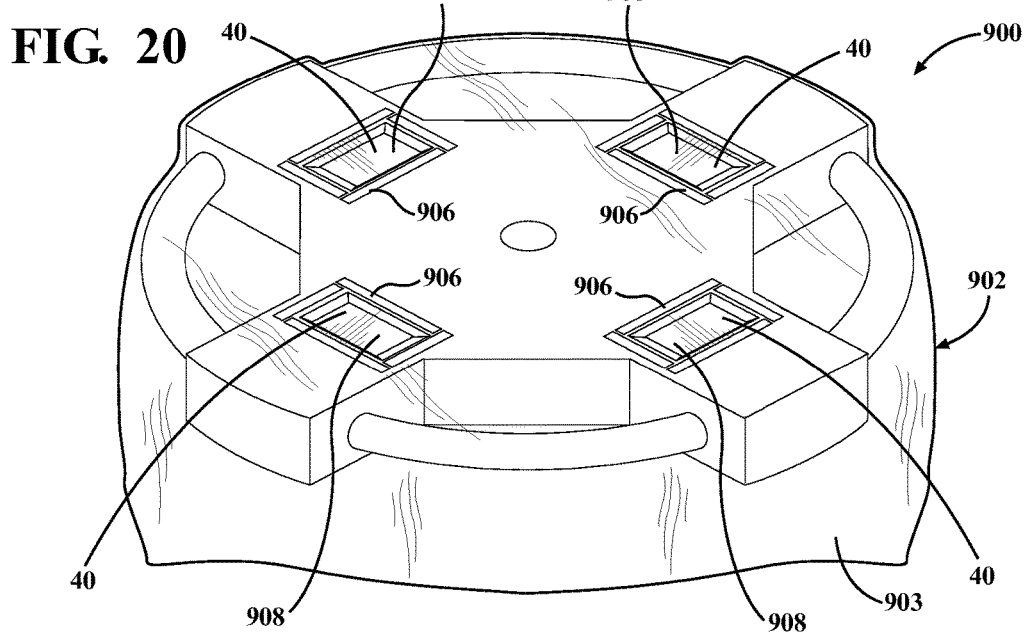
FIG. 20 is a perspective view of the camera assembly of FIG. 19 with the drape assembled to the camera unit.

With reference to FIGS. 19 and 20, a ninth embodiment of a camera and drape assembly 900 positions a drape 902 on a casing 938 of the camera unit 936. The drape 902 includes a flexible section 903, i.e., a first section 903, and rigid sections 908, i.e., second sections 908. The rigid sections 908 provide windows through which light emitted by the tracking elements can be received by the optical sensors 40. The rigid sections 908 are spaced from one another and separated by the flexible section 903.

The camera unit 936 includes first coupling devices 904. The drape 902 includes second coupling devices 906 for coupling with the first coupling devices 904. In the embodiment shown the first coupling devices 904 are ferromagnetic mounts 904 fixed to the casing 938 and the second coupling devices 906 are magnets 906 fixed to the rigid sections 908 (or the ferromagnetic mounts 904 could be on the rigid sections 908 with the magnets 906 on the casing 938). The drape 902 is mounted to the camera unit 936 by magnetic attraction between the ferromagnetic mounts 904 and the magnets 906 to position the drape 902 relative to the camera unit 936 and to support the drape 902 on the camera unit 936.

The rigid sections 908 cover the optical position sensors 40 when the mounts 904 and magnets 906 couple to each other so that the windows are aligned with the optical position sensors 40 to enable proper light detection from the tracking elements.

The flexible section 903 is formed of highly flexible, transparent film or foil such as polyethylene film. The rigid sections 908 are formed of a plastic sheet that is rigid relative to the flexible section 903 and is transparent. The flexible section 903 defines cutouts that receive the rigid sections 908. The rigid sections 908 are fixed to the flexible section 903 in the cutout by, for example, bonding, adhesive, tape, etc.

The engagement of the mounts 904 and magnets 906 provides tactile confirmation that the drape 902 is properly positioned relative to the camera unit 936.

With reference to FIGS. 21, 22, and 22A, a tenth embodiment of a camera and drape assembly 1000 positions a drape 1002 on a casing 1038 of the camera unit 1036.

The drape 1002 includes a flexible section 1003, i.e., a first section 1003, and rigid sections 1006, i.e., second sections 1006. The rigid sections 1006 provide windows 1010 through which light emitted by the tracking elements can be received by the optical sensors 40. The rigid sections 1006 are spaced from one another and separated by the flexible section 1003. The rigid sections 1006 are fixed to the flexible section 1003.

Bases 1004 are fixed to and extend from the casing 1038 peripherally about the optical position sensors 40. The rigid sections 1006 are configured to engage the bases 1004 by acting as covers for the bases 1004.

First coupling devices 1008 are coupled to the bases 1004. The drape 1002 includes second coupling devices 1012 for coupling to the first coupling devices 1008. In the embodiment shown, the first coupling devices 1008 are clamps 1008 (or latches) and the second coupling devices are protrusions 1012 that act as a catch for the clamps 1008. The clamps 1008 and the protrusions 1012 are configured to releasably lock to each other. In the embodiment shown, the clamps 1008 are configured to pivot relative to the bases 1004 to engage detent pockets (not numbered) in the protrusions 1012 on the rigid sections 1006. More specifically, the clamps 1008 are fixed to pivot shafts (not numbered) supported in projections on the bases 1004 (see FIG. 22A). The clamps 1008 are thereby capable of pivoting about their pivot shafts into engagement with the detent pockets in the protrusions 1012.

The rigid sections 1006 each include a transparent planar section that defines the window 1010 aligned with the optical position sensors 40 when the rigid sections 1006 are engaged with the bases 1004. The engagement of the rigid sections 1006 with the bases 1004 positions the drape 1002 relative to the camera unit 1036 and supports the drape 1002 on the camera unit 1036. The rigid sections 1006 also include a peripheral wall 1011 that depends downwardly from the window 1010 and is sized to fit about an upper rim of the bases 1004 when the rigid sections 1006 are mounted to the bases 1004. The windows 1010 may be integrally formed with the peripheral wall 1011 or may be separate (as shown) and fixed to the peripheral wall 1011 by adhesive, bonding, ultrasonic welding, or other methods.

In the embodiment shown, the flexible section 1003 of the drape 1002 is fixed to the peripheral wall 1011 such that part of the peripheral wall 1011, including the portion with the protrusions 1012, extends below the flexible section 1003. As a result, the clamps 1008 are able to engage the protrusions 1012 by pivoting over the protrusions 1012 and friction fitting into place without pinching the flexible section 1003 therebetween. Detent pockets on the protrusions 1012 facilitate this engagement, as shown in FIG. 22A. In other embodiments, the rigid sections 1006 may be fixed to the flexible section 1003 such that the peripheral wall 1011, including the protrusions 1012, at least partly extends above the flexible section 1003 so that the clamps 1008 engage the protrusions 1012 through the flexible section 1003.

The flexible section 1003 is formed of high flexible, transparent film or foil such as polyethylene film. The rigid sections 1006 are formed of a plastic that is rigid relative to the flexible section 1003. The entire rigid section 1006 may be transparent or only the windows 1010 may be transparent. The flexible section 1003 defines cutouts that receive the rigid sections 1006. The rigid sections 1006 are fixed to the flexible section 1003 in the cutouts by, for example, bonding, adhesive, tape, etc.

The engagement of the rigid sections 1006 with the bases 1004 provides tactile confirmation that the drape 1002 is properly positioned relative to the camera unit 1036. The rigid sections 1006 can include colored borders to identify the portion of the rigid sections 1006 that engage the bases 1004. The engagement of the clamps 1008 to the protrusions 1012 ensures that the windows 1010 remain in alignment with the optical sensors 40.

With reference to FIGS. 23, 24, and 24A, an eleventh embodiment of a camera and drape assembly 1100 positions a drape 1102 on a casing 1138 of the camera unit 1136. The drape 1102 includes a flexible section 1103, i.e., a first section 1103, and rigid sections 1106, i.e., second sections 1106. The rigid sections 1106 provide windows 1108 through which light emitted by the tracking elements can be received by the optical sensors 40. The rigid sections 1106 are spaced from one another and separated by the flexible section 1103. The rigid sections 1106 are fixed to the flexible section 1103.

Bases 1104 are fixed to and extend from the casing 1138 peripherally about the optical position sensors 40. The rigid sections 1106 are configured to engage the bases 1104 by acting as covers or caps for the bases 1004. In this embodiment, the bases 1104 are first coupling devices fixed to and extending from the outer casing 1138 circumferentially about the optical position sensors 40.

The rigid sections 1106 are configured to engage the bases 1104 to position the drape 1102 relative to the camera unit 1136 and to support the drape 1102 on the camera unit 1136. The rigid sections 1106 include a downwardly extending cap wall 1110 that defines a recess to receive rims of the bases 1104. In this embodiment, the cap walls 1110 are second coupling devices 1110 configured to couple to the bases 1104. The bases 1104 are configured such that the rigid sections 1106 are retained on the bases 1104 by a friction fit between the bases and the cap walls 1110.

The rigid sections 1106 each include a transparent planar section that defines the window 1108. Each of the windows 1108 is fixed to one of the cap walls 1110. The windows 1108 may be integrally formed with the cap walls 1110 or may be separate (as shown) and fixed to the cap walls 1110 by adhesive, bonding, ultrasonic welding, or other methods. The windows 1108 are aligned with the optical position sensors 40 when the rigid sections 1106 are engaged with the bases 1104. The engagement of the rigid sections 1106 with the bases 1104 positions the drape 1102 relative to the camera unit 1136 and supports the drape 1102 on the camera unit 1136.

The flexible section 1103 of the drape 1102 is formed of highly flexible, transparent film or foil such as polyethylene film. The rigid sections 1106 are formed of a plastic that is rigid relative to the flexible section 1103. The entire rigid section 1106 may be transparent or only the windows 1108 may be transparent. The flexible section 1103 defines cutouts that receive the rigid sections 1106. The rigid sections 1106 are fixed to the flexible section 1103 in the cutouts by, for example, bonding, adhesive, tape, etc.

The engagement of the rigid sections 1106 with the bases 1104 provides visual and tactile confirmation that the drape 1102 is properly positioned relative to the camera unit 1136.

With reference to FIGS. 25, 26, and 26A, a twelfth embodiment of a camera and drape assembly 1200 positions a drape 1202 on a casing 1238 of the camera unit 1236. The drape 1202 includes a flexible section 1203, i.e., a first section 1203, and rigid sections 1205, i.e., second sections 1205. The rigid sections 1205 provide windows 1206 through which light emitted by the tracking elements can be received by the optical sensors 40. The rigid sections 1205 are spaced from one another and separated by the flexible section 1203. The rigid sections 1205 are fixed to the flexible section 1203.

Bases 1204 are fixed to and extend from the casing 1238 peripherally about the optical position sensors 40. The rigid sections 1205 are configured to engage the bases 1204 by acting as covers or caps for the bases 1204. Specifically, the bases 1204 and the rigid sections 1205 are configured to friction fit or snap-fit to each other.

The rigid sections 1205 include a transparent top that defines the window 1206 and transparent sides extending from the transparent top to a peripheral rim 1208. The rim 1208 is configured to engage the base 1204 in a friction fit. The bases 1204 include mating peripheral channels 1211. The channels 1211 and rims 1208 are the first and second coupling devices 1211, 1208 in this embodiment. The rims 1208 are retained in the channels 1211 by an interlocking friction fit. The engagement of the rigid sections 1205 with the bases 1204 positions the drape 1202 relative to the camera unit 1236 and supports the drape 1202 on the camera unit 1236.

The flexible section 1203 is formed of highly flexible, transparent film or foil such as polyethylene film. The rigid sections 1205 are formed of a plastic that is rigid relative to the flexible section 1203. The flexible section 1203 defines cutouts that receive the rigid sections 1205. The rigid sections 1205 are fixed to the flexible section 1203 in the cutouts by, for example, bonding, adhesive, tape, etc. The flexible section 1203 may be attached to the rigid sections 1205 above the rims 1208 (as shown in FIG. 26A) so that the rims 1208 are able to engage the channels 1211 without pinching the flexible section 1203 therebetween. In this case, the flexible section 1203 is attached to the top or sides of the rigid sections 1205 by bonding, adhesive, tape, etc.

The engagement of the rigid sections 1205 with the bases 1204 provides visual and tactile confirmation that the drape 1202 is properly positioned relative to the camera unit 1236. The rigid sections 1205 can include colored borders to identify the portion of the rigid sections 1205 that engage the bases 1204.

Figure 27:
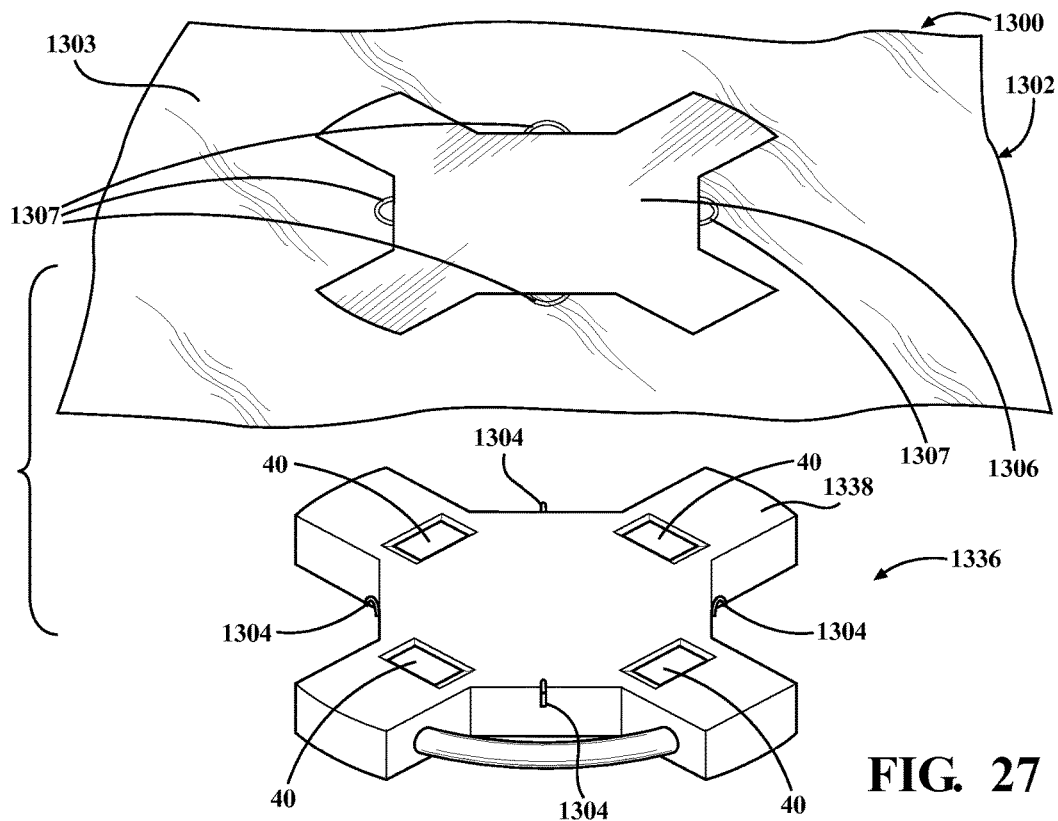
FIG. 27 is a partially exploded view of a thirteenth embodiment of the camera assembly including a camera unit and a drape.
Figure 28:
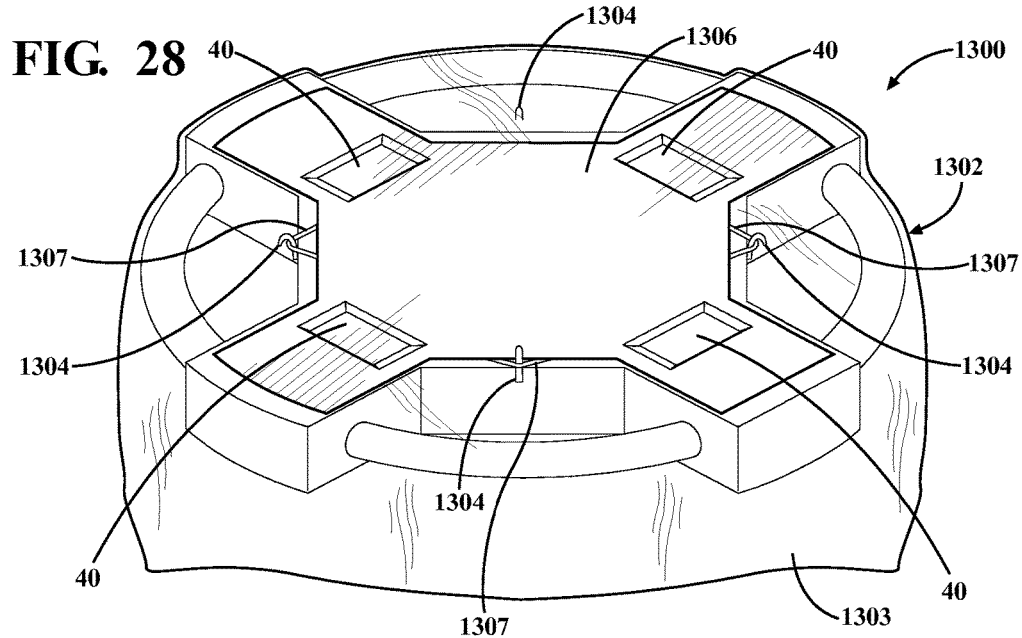
FIG. 28 is a perspective view of the camera assembly of FIG. 27 with the drape assembled to the camera unit.

With reference to FIGS. 27-28, a thirteenth embodiment of a camera and drape assembly 1300 positions a drape 1302 on an outer casing 1338 of the camera unit 1336. The drape 1302 includes a flexible section 1303, i.e., a first section 1303, and a rigid section 1306, i.e., second sections 1306. The rigid sections 1306 provide a window through which light emitted by the tracking elements can be received by the optical sensors 40. The rigid section 1306 is fixed to the flexible section 1303. In the embodiment shown, the rigid section 1306 has a center portion and a plurality of wings (four shown) that extend outwardly from the center portion. The rigid section 1306 is planar.

First coupling devices 1304 are fixed to the outer casing 1338 of the camera unit 1336 to engage the drape 1302 to position the drape 1302 relative to the camera unit 1336 and support the drape 1302 on the camera unit 1336. In this embodiment, the first coupling devices are retainers in the form of hooks 1304.

Elastic bands 1307 are coupled to the rigid section 1306. The elastic bands 1307 engage the hooks 1304 to retain, and position, the rigid section 1306 over and across the optical sensors 40. The rigid section 1306 covers the optical position sensors 40 when the elastic bands 1307 are engaged with the hooks 1304. The engagement of the elastic bands 1307 with the hooks 1304 provide visual and tactile confirmation that the drape 1302 is properly positioned relative to the camera unit 1336.

The flexible section 1303 is formed of highly flexible, transparent film or foil such as polyethylene film. The rigid section 1306 is formed of a plastic sheet that is rigid relative to the flexible section 1303 and is transparent. The flexible section 1303 defines a cutout that receives the rigid section 1306. The rigid section 1306 is fixed to the flexible section 1303 in the cutout by, for example, bonding, adhesive, tape, etc. The elastic bands 1307 are fixed to a bottom surface of the rigid section 1306 beneath the flexible section 1303 so that the elastic bands 1307 are able to engage the hooks 1304 without trapping the flexible section 1303 therebetween.

The camera units 36, 236, 336, 436, 536, 636, 736, 836, 936, 1036, 1136, 1236, 1336 disclosed herein are all similarly configured to communicate with tracking elements such as the LEDs 50 to determine the position and/or orientation of objects in the operating room. Each of the camera units 36, 236, 336, 436, 536, 636, 736, 836, 936, 1036, 1136, 1236, 1336 include a plurality of the optical sensors 40 supported by their casings and exposed through their casings for detecting the tracking elements. Each of the camera units 36, 236, 336, 436, 536, 636, 736, 836, 936, 1036, 1136, 1236, 1336 includes the camera controller 42 in communication with the optical sensors 40 to receive signals from the optical sensors 40.

It should be appreciated that features associated with the different embodiments disclosed herein could be combined in other embodiments. It should also be appreciated that the drapes 102, 202, 302, 402, 502, 602, 702, 802, 902, 1002, 1102, 1202, 1302 are provided sterile such as by conventional sterilization methods to be used in the operating room to separate the camera units 36, 236, 336, 436, 536, 636, 736, 836, 936, 1036, 1136, 1236, 1336 from the sterile field.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A camera and drape assembly for use with a tracking element of a surgical system, said camera and drape assembly comprising:
    a camera unit including a casing and a plurality of optical sensors supported by said casing for detecting the tracking element; and
    a drape including a flexible section and a plurality of windows that are rigid relative to said flexible section and surrounded by said flexible section, said windows being planar and generally rectangular;
    wherein said camera unit further includes a plurality of first coupling devices disposed peripherally about said optical sensors and said drape includes a plurality of second coupling devices for coupling to said first coupling devices to align said windows over said optical sensors so that said optical sensors are capable of receiving light from the tracking element through said windows.

2. The camera and drape assembly of claim 1, wherein said second coupling devices are configured to provide tactile confirmation that said drape is properly positioned relative to said camera unit when said second coupling devices are coupled to said first coupling devices.

3. The camera and drape assembly of claim 1, wherein said first coupling devices and said second coupling devices are configured to engage each other in a snap-fit connection.

4. The camera and drape assembly of claim 1, wherein said windows are transparent.

5. The camera and drape assembly of claim 1, wherein said first coupling devices and said second coupling devices are generally rectangular.

6. The camera and drape assembly of claim 1, wherein said plurality of first coupling devices include a plurality of walls disposed about said optical sensors and said windows are arranged to abut said walls when said second coupling devices are coupled to said first coupling devices.

7. The camera and drape assembly of claim 1, wherein said plurality of second coupling devices include a plurality of peripheral walls with said windows being separate from and fixed to said peripheral walls.

8. The camera and drape assembly of claim 1, wherein said second coupling devices include a plurality of colored borders.

9. A surgical drape for use with a camera unit having a casing, a plurality of optical sensors supported by the casing, and a plurality of first coupling devices, said surgical drape comprising:
    a flexible section and a plurality of windows that are rigid relative to said flexible section and surrounded by said flexible section, said windows being planar and generally rectangular; and
    a plurality of second coupling devices configured to couple to said first coupling devices to align said windows over the optical sensors so that the optical sensors are capable of receiving light from a tracking element through said windows.

10. The surgical drape of claim 9, wherein said second coupling devices are configured to provide tactile confirmation that the surgical drape is properly positioned relative to the camera unit when said second coupling devices are coupled to the first coupling devices.

11. The surgical drape of claim 9, wherein said second coupling devices are configured to engage the first coupling devices in a snap-fit connection.

12. The surgical drape of claim 9, wherein said windows are transparent.

13. The surgical drape of claim 9, wherein said second coupling devices are generally rectangular.

14. The surgical drape of claim 9, wherein said windows are arranged to abut a plurality of walls of the first coupling devices when said second coupling devices are coupled to the first coupling devices.

15. The surgical drape of claim 9, wherein said plurality of second coupling devices include a plurality of peripheral walls with said windows being separate from and fixed to said peripheral walls.

16. The surgical drape of claim 9, wherein said second coupling devices include a plurality of colored borders.

* * * * *